(12) United States Patent
Zhang

(10) Patent No.: US 9,293,023 B2
(45) Date of Patent: Mar. 22, 2016

(54) TECHNIQUES FOR EMERGENCY DETECTION AND EMERGENCY ALERT MESSAGING

(71) Applicant: Jack Ke Zhang, Ijamsville, MD (US)

(72) Inventor: Jack Ke Zhang, Ijamsville, MD (US)

( * ) Notice: Subject to any disclaimer, the term of this patent is extended or adjusted under 35 U.S.C. 154(b) by 0 days.

(21) Appl. No.: 14/661,834

(22) Filed: Mar. 18, 2015

(65) Prior Publication Data

US 2015/0269824 A1 Sep. 24, 2015

Related U.S. Application Data

(63) Continuation-in-part of application No. 14/591,782, filed on Jan. 7, 2015, which is a continuation of application No. 14/218,888, filed on Mar. 18, 2014, now Pat. No. 8,952,818.

(51) Int. Cl.
| | |
|---|---|
| *G08B 21/04* | (2006.01) |
| *A61B 5/11* | (2006.01) |
| *A61B 5/00* | (2006.01) |

(52) U.S. Cl.
CPC .......... *G08B 21/0438* (2013.01); *A61B 5/0022* (2013.01); *A61B 5/1117* (2013.01); *G08B 21/0446* (2013.01); *G08B 21/0453* (2013.01); *A61B 5/746* (2013.01)

(58) Field of Classification Search
CPC ..................... A61B 5/1117; A61B 2562/0219; A61B 5/0205; A61B 5/0022; A61B 5/1118; A61B 5/681; A61B 5/1116; G08B 21/0446; G08B 21/043; G08B 21/0453; G08B 21/02; G08B 25/016

See application file for complete search history.

(56) References Cited

U.S. PATENT DOCUMENTS 5,827,180 A 10/1998 Goodman et al.
6,075,755 A 6/2000 Zarchan
(Continued)

FOREIGN PATENT DOCUMENTS

JP 2007505412 3/2007
KR 1020020013214 2/2002

OTHER PUBLICATIONS

U.S. Appl. No. 14/218,821, filed Mar. 18, 2014, Titled: Techniques for Monitoring Prescription Compliance Using a Body-Worn Device.
(Continued)

*Primary Examiner* — James Yang
(74) *Attorney, Agent, or Firm* — Kilpatrick Townsend & Stockton LLP

(57) ABSTRACT

A method, apparatus, and/or system for monitoring a user and transmitting an emergency notification is disclosed. The apparatus can monitor a user's overall wellness and adherence to a therapy regimen. The apparatus can also detect a variety of emergency situations affecting the user. For example, the apparatus can detect a fall affecting the user, the activation of an emergency indicator by the user, or an emergency based on vital signs and the overall wellness of the user. The apparatus can generate and transmit an alert notification in response to determining an emergency is affecting the user. The apparatus can select the form of the alert and the network on which to transmit the alert. The apparatus can determine the form of the alert and the network based on the severity of the emergency and the strength of the networks available to the apparatus. The form of the alert and the transmission network selected can optimize the likelihood of the alert notification being successfully transmitted.

7 Claims, 19 Drawing Sheets

(56) References Cited

U.S. PATENT DOCUMENTS

| | | | |
|---|---|---|---|
| 6,443,906 B1 | 9/2002 | Ting et al. | |
| 7,162,368 B2 | 1/2007 | Levi et al. | |
| 7,242,306 B2 * | 7/2007 | Wildman | A61B 5/1113 340/539.16 |
| 7,285,090 B2 | 10/2007 | Stivoric et al. | |
| 8,217,795 B2 | 7/2012 | Carlton-Foss | |
| 8,457,367 B1 | 6/2013 | Nechyba et al. | |
| 8,461,988 B2 * | 6/2013 | Tran | G06F 19/3418 340/3.1 |
| 8,708,903 B2 * | 4/2014 | Tran | A61B 5/021 600/300 |
| 8,952,818 B1 | 2/2015 | Zhang | |
| 2002/0026330 A1 | 2/2002 | Klein et al. | |
| 2003/0052787 A1 | 3/2003 | Zerhusen et al. | |
| 2003/0060721 A1 | 3/2003 | Nakazawa et al. | |
| 2003/0176815 A1 | 9/2003 | Baba et al. | |
| 2003/0212379 A1 | 11/2003 | Bylund et al. | |
| 2004/0077934 A1 | 4/2004 | Massad | |
| 2005/0089197 A1 | 4/2005 | Iwasaki et al. | |
| 2005/0101845 A1 | 5/2005 | Nihtila et al. | |
| 2007/0197878 A1 | 8/2007 | Shklarski et al. | |
| 2007/0257636 A1 | 11/2007 | Phillips et al. | |
| 2008/0086318 A1 | 4/2008 | Gilley et al. | |
| 2008/0129518 A1 | 6/2008 | Carlton-Foss et al. | |
| 2008/0162192 A1 | 7/2008 | Vonk et al. | |
| 2008/0266118 A1 | 10/2008 | Pierson et al. | |
| 2009/0187121 A1 | 7/2009 | Evans et al. | |
| 2009/0252311 A1 | 10/2009 | Kuiken | |
| 2009/0318779 A1 | 12/2009 | Tran | |
| 2009/0322513 A1 | 12/2009 | Hwang et al. | |
| 2009/0322540 A1 | 12/2009 | Richardson et al. | |
| 2009/0322548 A1 | 12/2009 | Gottlieb et al. | |
| 2010/0010428 A1 | 1/2010 | Yu et al. | |
| 2010/0076331 A1 | 3/2010 | Chan et al. | |
| 2010/0152548 A1 | 6/2010 | Koski et al. | |
| 2010/0194572 A1 | 8/2010 | Chan et al. | |
| 2011/0093296 A1 | 4/2011 | Klink | |
| 2011/0230733 A1 | 9/2011 | Al-Ali et al. | |
| 2011/0263950 A1 | 10/2011 | Larson et al. | |
| 2012/0274464 A1 | 11/2012 | Sweeney et al. | |
| 2013/0127980 A1 | 5/2013 | Haddick et al. | |
| 2013/0169431 A1 | 7/2013 | Alhuwaishel et al. | |
| 2013/0310658 A1 | 11/2013 | Ricks et al. | |
| 2013/0318027 A1 | 11/2013 | Almogy et al. | |
| 2013/0345530 A1 | 12/2013 | McRoberts et al. | |
| 2014/0052464 A1 | 2/2014 | Ray et al. | |
| 2014/0163400 A1 | 6/2014 | Khanuja et al. | |
| 2014/0247361 A1 | 9/2014 | Sarwar et al. | |
| 2014/0275928 A1 | 9/2014 | Acquista et al. | |
| 2014/0276552 A1 | 9/2014 | Nguyen, Jr. et al. | |
| 2014/0375246 A1 | 12/2014 | Boysen, III et al. | |
| 2014/0378786 A1 | 12/2014 | Hong et al. | |

OTHER PUBLICATIONS

U.S. Appl. No. 14/218,888, Notice of Allowance, mailed Sep. 19, 2014, 18 pages.

U.S. Appl. No. 14/565,373, filed Dec. 9, 2014, Titled: Techniques for Power Source Management Using a Wrist-Worn Device.

U.S. Appl. No. 14/565,384, filed Dec. 9, 2014, Titled: Techniques for Near Real Time Wellness Monitoring Using a Wrist-Worn Device.

U.S. Appl. No. 14/591,782, filed Jan. 7, 2015, Titled: Emergency Detection and Alert Apparatus With Floor Elevation Learning Capabilities.

U.S. Appl. No. 14/703,291, filed May 4, 2015, Titled: Managing Multi-User Access to Controlled Locations in a Facility.

Blipcare , "Wi-Fi Blood Pressure", retrieved with the Wayback Machine with http://www.blipcare.com/blip-bp.html, Feb. 4, 2013, 4 pages.

U.S. Appl. No. 14/591,782 , "Non-Final Office Action", mailed Aug. 21, 2015, 8 pages.

PCT/US2015/021335 , "International Search Report and written opinion", mailed Jun. 29, 2015, 21 pages.

U.S. Appl. No. 14/591,782 , "Notice of Allowance", mailed Nov. 12, 2015, 10 pages.

U.S. Appl. No. 14/591,782 , "Supplemental Notice of Allowance", mailed Dec. 3, 2015, 3 pages.

* cited by examiner

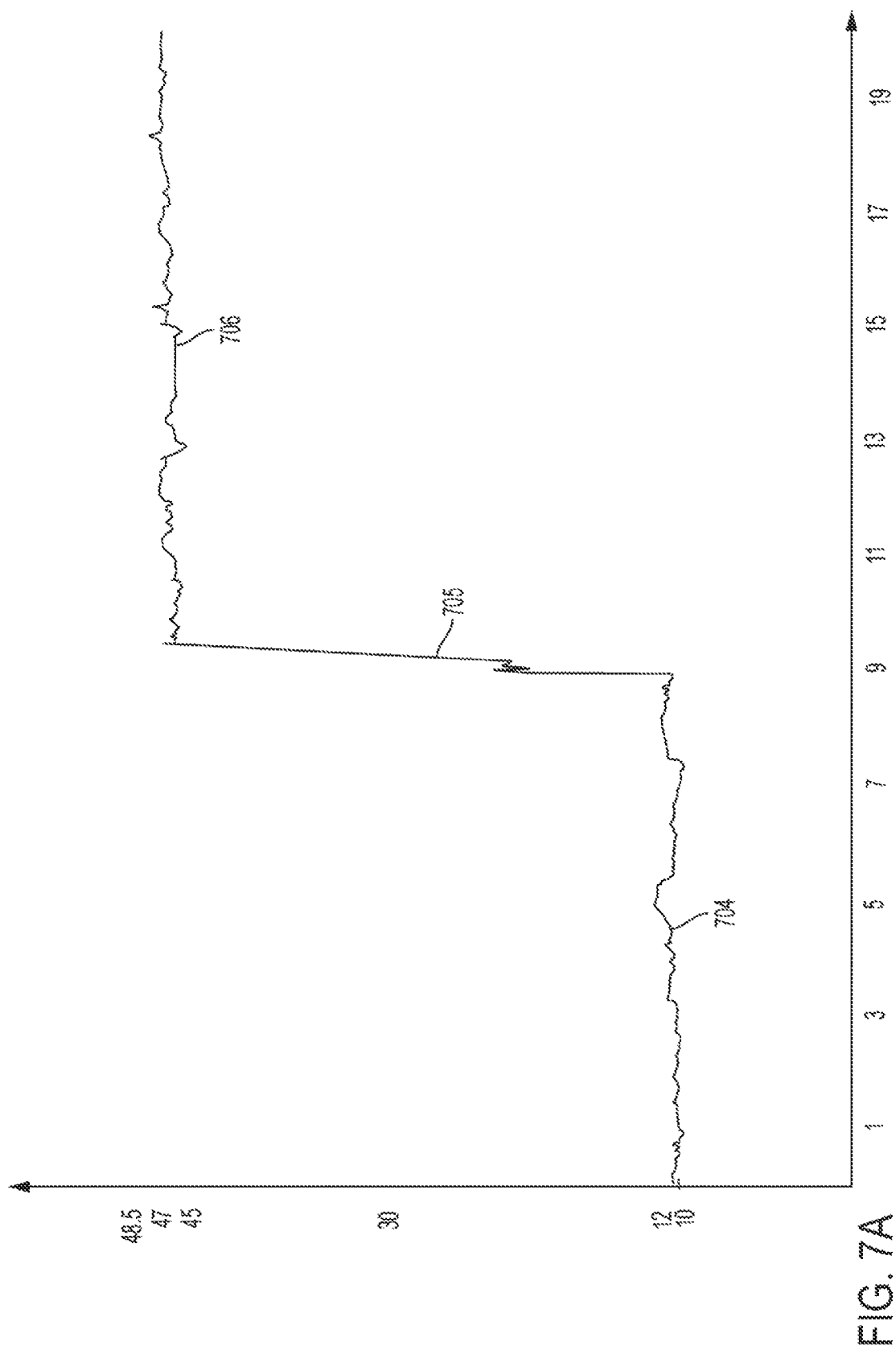

TECHNIQUES FOR EMERGENCY DETECTION AND EMERGENCY ALERT MESSAGING

CROSS REFERENCE TO RELATED APPLICATIONS

The present application is a continuation-in-part of U.S. patent application Ser. No. 14/591,782, filed Jan. 7, 2015, which is a continuation of U.S. patent application Ser. No. 14/218,888, filed Mar. 18, 2014, now issued as U.S. Pat. No. 8,952,818 on Feb. 10, 2015, and is related to PCT Application No. PCT/US2015/021335 filed on Mar. 18, 2015, each of which is incorporated herein by reference in its entirety.

BACKGROUND

Aspects of the disclosure relate to an emergency detection device with wireless alert capabilities and location reporting.

Certain individuals may be vulnerable to emergency medical situations resulting from unexpected falls, fainting, collapse, drops or spikes in blood pressure, oxygen saturation, heart rate, and other health related situations. These individuals include the elderly, medicating patients and other individuals who suffer from heart conditions, epilepsy or other such medical problems.

Devices for detecting falls have been used for some time. Most of these devices are worn by an individual at risk of falling. However, detecting falls can be a complicated problem because data registered during a fall may be affected by noise or may be similar to data generated when the wearer performs certain commonplace actions. Also, because people vary greatly with regards to height, weight and activity level, the data generated when one individual suffers a fall may be significantly different than the data generated by when other people suffer falls. For these reasons, conventional fall detectors are highly susceptible to failures when a fall occurs, as well as false-positive fall detections. In addition, while devices for monitoring a wearer's vital signs have been used, the devices' techniques for notifying emergency personnel that an emergency situation is affecting the wearer are limited. The devices' often rely on wireless signals or other potentially unavailable communication means. In addition, even when an alert is successfully transmitted indicating an emergency situation has occurred, additional information about the emergency affecting the wearer and the wearer's health may not be available. For these reasons, conventional emergency alert devices fail to consistently notify emergency personnel when an emergency affects the wearer. Nor do they provide data sufficient to evaluate the type of emergency that is affecting the user.

BRIEF SUMMARY

This disclosure describes a wearable emergency detection apparatus configured to facilitate monitoring a wearer of the apparatus and techniques for transmitting alert notifications when an emergency situation affecting the wearer is detected. Emergency situations can include, (a) a fall detected by the apparatus, (b) activation of an emergency indicator by the wearer, and (c) an emergency detected by the apparatus based on wellness monitoring.

The apparatus comprises a first sensor configured to generate elevation data that represents an elevation of the apparatus, a second sensor configured to generate acceleration data that represents a magnitude of acceleration of the apparatus, a processor configured to, determine, based on the elevation data, an elevation of a floor located underneath the wearer, and detect a fall affecting the wearer, wherein detecting a fall includes, determining that the acceleration data satisfies a fall hypothesis condition, determining, based on the elevation data, that the apparatus is vertically displaced from the floor by less than a threshold distance.

The apparatus can include a first sensor component configured to generate a first signal used to determine an elevation of the apparatus, and a second sensor configured to generate a second signal, wherein the second signal is used to determine location. The apparatus also includes a processor configured to estimate an elevation of a surface located underneath the person, wherein estimating is based on the first signal and the second signal, and detect a fall affecting the person, wherein detecting a fall includes determining, based on the elevation data, that the apparatus is within a threshold distance of one of the surfaces. A transmitter within the apparatus is configured to transmit an alert in response to a fall detected by the processor. The apparatus can also comprise an emergency indicator (e.g., a button or a touch screen) that can be activated by the wearer to indicate the wearer is experiencing an emergency. The apparatus can be configured to generate and transmit an alert notification in response to detecting the emergency indicator has been activated.

This apparatus can also be configured to monitor various vital signs of the wearer via one or more sensors. The apparatus can includes such sensors, for example but without limitation, a blood-oxygen level sensor(s), hear rate monitor(s), blood pressure monitor(s), glucose monitor(s), pedometer(s), thermometer(s), and the like. The sensors can provide readings used to provide wellness monitoring as described herein.

This disclosure also describes systems, methods and computer-program products in which the inventive elements, techniques and process herein disclosed may be embodied. The system, method and computer-program product may be for monitoring a person wearing a device, the device having multiple sensors disposed therein. The system and computer-program product may be configured to perform certain of the following processes which also may characterize the aforementioned method. The processes involve generating elevation data that represents an elevation of the device, generating acceleration data that represents a magnitude of acceleration of the device, determining, based on the elevation data, an elevation of a floor located underneath the person and detecting a fall affecting the person, wherein detecting the fall includes determining that the acceleration data satisfies a fall condition, determining, based on the elevation data, that the apparatus is vertically displaced from the floor by less than a threshold distance, and transmitting an alert in response to a fall detected by the processor. The processes can also involve generating sensor data that represents a vital sign monitored by the sensor, storing the sensor data, and determining based on the sensor data if an emergency situation is affecting the wearer.

BRIEF DESCRIPTION OF THE DRAWINGS

Aspects of the disclosure are illustrated by way of example. In the accompanying figures, like reference numbers indicate similar elements.

FIGS. 7A and 7B presents examples of patterns in elevation data which the monitoring device may recognize in order to determine elevations of surfaces and floors beneath a wearer.

DETAILED DESCRIPTION

Figure 1A:
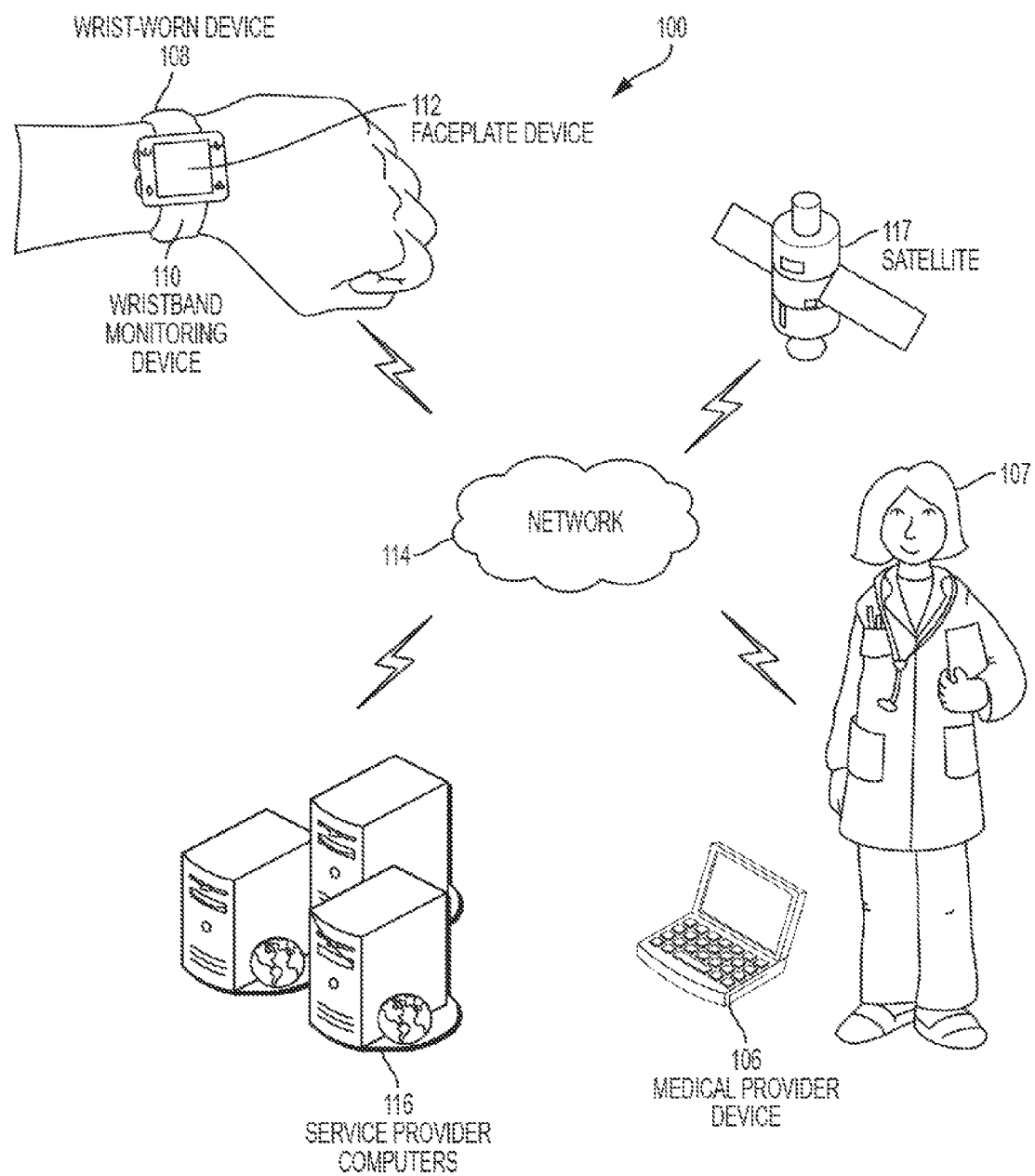
FIG. 1A illustrates a simplified diagram of an example operating environment in which the emergency detection and notification device of this disclosure may be commonly used.

This disclosure describes an emergency detection and monitoring device configured to be worn on the human body (e.g., a watch). The monitoring device includes sensory, communications, processing and software components that provide functionality for executing any number of the techniques, processes or methods (hereinafter the term "disclosed procedures" will refer to the techniques, processes and methods) which are described in this disclosure. The disclosed features enable the monitoring device to detect an emergency situation affecting the wearer of the monitoring device and inform emergency medical personnel when an emergency situation is detected.

The monitoring device may be configured as a wrist-worn device or other similar accessory suitable for attachment on the user's arm or at any other location on the body. The monitoring device includes sensors and wireless communication interfaces that gather or receive data used by the monitoring device to monitor the wearer's condition and learning about the environment in which the monitoring device is being operated. The monitoring device monitors the wearer's condition for example, by determining whether the wearer has potentially fallen, monitoring the overall wellness of the wearer (e.g., based on sensor data), and monitoring an emergency indicator that may be activated by the wearer.

The monitoring can be performed internally by a processor within the monitoring device which analyzes data from one or more sensors, stores historical data statistics and summary information, and learns about the wearer and monitoring device operating environment based on the data and inputs provided by the wearer. Certain learning, data storage, and analytical procedures may additionally or alternatively be performed at a server with which the monitoring device is configured to communicate.

The monitoring device can include fall detection sensors (e.g., an altimeter, a thermometer, and an accelerometer). The monitoring device can also include vital sign sensors (e.g., a heart rate sensor, a blood pressure sensor, a body temperature sensor, an oxygen saturation sensor, a glucose sensor, and any other sensors that can generate data related to the health of the wearer). The monitoring device can also include a GPS or other feature for precisely determining location, as well as a clock. In subsequent paragraphs, the term sensor will be used to refer to any of these instruments, including the GPS and the clock. Hereinafter, the "wearer's condition" or condition relates to the wearer's medical state, including whether the wearer has fallen.

The altimeter, accelerometer, and GPS periodically provide data representing the elevation, acceleration, and geographic location of the monitoring device. So that the monitoring device may detect when it is being worn, the thermometer measures the temperature at the monitoring device surface that contacts the wearer's body when the monitoring device is being worn. A digital clock is used to generate a time stamp for each of the data observations generated by the sensors. The time stamps are used by the processor in the analysis of sensor data, and facilitate pattern recognition and improved capacity for determining the operational environment of the monitoring device.

The monitoring device includes intelligent learning capability that involves analyzing GPS data and timestamps to learn the location of buildings in which the user spends significant amounts of time. When a building is recognized in this way, the monitoring device further stores and analyzes altimeter and temperature data registered for so long as the device continues to sense that it is within the building. In this analysis, the monitoring device learns the elevations of significant surfaces such as floors, tables, and desks. The monitoring device stores the elevation information for use in detecting falls when the wearer and device are within the building.

By learning elevations of surfaces in a building, the monitoring device is able to later compare recent elevation data to the learned elevations when acceleration indicative of a fall is detected within the building. Any such comparison may serve to confirm a fall when the elevation indicated by the recent data is approximately commensurate with the elevation of a floor in the building. Conversely, the monitoring device determines that a fall has not occurred when the elevation indicated by the recent data is not commensurate with any learned floor elevation in the building.

The monitoring device includes a touchscreen, button or keypad interface, or other similar interface. The interface facilitates soliciting information from the wearer, and obtaining input data and information provided by the wearer in response. The monitoring device solicits information about the wearer or the wearer's condition or environment so as to improve its fall detection analysis and avoid false positive detections. For example, the monitoring device uses wearer inputs to obtain information about the wearer's physique, lifestyle, health, activity level and other information relevant to fall detection. The monitoring device further solicits any wearer inputs that may facilitate improved learning, analysis and sensing performed by the monitoring device. For example, when the monitoring device detects that position and elevation information is approximately unchanged throughout an evening, the monitoring device may solicit the wearer to confirm that he is at home, or on a specific floor of his house. The monitoring device may store inputted confirmations or information in memory, as well as modify its analysis of sensor data based on the information provided by the inputs.

The touchscreen or interface is also used to communicate with the wearer when a fall is detected. By communicating with the wearer, the monitoring device obtains information that confirms the occurrence of a fall or indicates that a false positive detection has occurred. By facilitating user communications to override the detection of falls, unnecessary alerts to medical dispatching or emergency services is avoided.

In some aspects, the monitoring device is preconfigured with information regarding at least one therapy. For instance, the monitoring device is preconfigured to be used for a blood pressure therapy. As used herein, a "therapy" may include one or more medical treatments including, but not limited to, one or more prescribed medications, one or more physical activities, one or more sensor reading requirements, or any combination of the above. In at least one example, information is loaded onto the monitoring device by a physician, a pharmacist, or another service provider. The pre-loaded information is then used to determine a regimen to be followed. A "regimen," as used herein, is intended to mean a schedule specifying at least one situation for which at least one event associated with a therapy should be performed. For instance, a regimen may indicate that an event (e.g. medication intake, exercise commencement, sensor reading commencement) should occur at pre-determined periodic times. Additionally, the monitoring device may activate sensor reading intake based on the regime, by user-initiation, or in response to determining an emergency is affecting the user.

In accordance with at least one embodiment, the monitoring device receives user input indicating compliance with the therapy. For instance, the user may be reminded to eat prior to taking his medication. Subsequent to the reminder being presented to the user, the user may be prompted for input. The prompt may be included in the reminder or may exist as a separate prompt. In at least one example, the reminder constitutes a textual message presented on the faceplate device and/or an audible alert sounded by the faceplate device. The user acknowledges the reminder by dismissing the reminder and/or turning off the audible sound. In some cases, dismissing the reminder and/or turning off the audible sound may be considered user input indicating compliance with the reminder. In at least one example, the user is queried regarding his compliance. For instance, the user is posed the question "did you eat a meal?" The user enters input indicating either that he did eat a meal, or alternatively, that he did not eat a meal. In at least one example, a Bluetooth device is used to enter user input indicating compliance with the reminder. For instance, a medication container having Bluetooth communication capabilities sends, to the watch, an indication that the medication container has been opened. This indication, alone or in combination with the reminder information, constitutes user input indicating that the user has complied with taking his medication.

In some aspects, the regimen dictates that the watch query the user with a question some period of time after the user has indicated that he has complied with the reminder. For instance, the regimen can specify that one hour after receipt of the user compliance input the user be asked, "Are you feeling dizzy?" The user makes a selection on the watch indicating a response to the question. The response is recorded by the watch and reported, wirelessly, away from the watch (e.g., to a server responsible for storing such information), or alternatively, stored on the watch.

In at least one aspect, the regimen causes a pressure sensor to be activated some period after the user compliance input has been received, and/or at another suitable time as defined by the regimen. The period between sensor activations may vary depending on the therapy and may further depend on user input. The watch records any sensor readings taken and reports the sensor readings away from the watch (e.g., to a server responsible for storing such information). Alternatively, the watch may store such sensor readings on the wrist-worn device.

In accordance with at least one aspect of the present disclosure, previously received user input is used to modify a regimen. User input, as described above, includes user actions taken in response to presented reminders, user actions taken regarding Bluetooth-enabled containers, user responses to questions posed by the watch, and/or a lack of a user response. User input may be recorded by the monitoring device at any suitable time. In at least one example, the monitoring device reports user input electronically to a physician and/or pharmacist, for example. This report may be reported in an email message, a text message, or any suitable type of electronic communication. Based on the report, or at any suitable time, the physician and/or pharmacist modify the prescribed therapy. This modification is electronically communicated to the monitoring device. In response to the modification, the monitoring device alters the therapy and/or regimen to reflect the modification. Additionally, or alternatively, the watch modifies the regimen based on the received user responses in accordance with the therapy. Alternatively, the monitoring device can indicate to the user that he should refrain from taking any more medication. A variety of modifications may be determined and would depend on the particular therapy being implemented and the user input received.

In accordance with at least one aspect of the present disclosure, the watch tracks sensor readings taken by one or more sensors located on the watch. These sensor readings may be manually initiated by the user or initiated based on the regimen. In some aspects, a wellness index may be calculated by a processor on the monitoring device. A "wellness index," as used herein is a numerical value that is calculated by weighing a number of inputs (e.g., user input, sensor readings), the inputs having various weights according to importance to overall health or specific to the therapy. The wellness index provides an overall assessment of the user's general health or wellness given the number of weighted inputs.

For example, in at least one embodiment, the wellness index may be calculated using a dynamically growing number of parameters passively monitored by the monitoring device, including at least one of the following: a body temperature value, a temperature trend, one or more non-purposeful movements, one or more purposeful activities patterns, a movement intensity, a movement quality, a restfulness, a blood oxygen value, a PulseOx trend, an amount of perspiration, or a determination of dehydration. Each passively monitored parameter listed above may carry a weighted value in the algorithm used to determine the wellness index. Additionally, non-passive information and data may be collected. Non-passive data may include affirmative user input typically requiring an act by the user (e.g., the pushing of a button), a body weight, a glucose level, a peak flow meter, a user's pulse profile taken manually, a heart rate/heart rhythm of a user. Non-passive data may be considered in the wellness index calculation to further refine the index. Further, user input collected to generate qualitative information may relate to questions regarding dietary activities, sensory perception, pain management, bowel/urinary activity, sleeping habits/quality, emotional health, cognitive abilities, etc. These answers may be used to capture the perspective of user.

In at least one aspect of the present disclosure, questions can be presented automatically (e.g., textually, or audibly) on the device based on time, or intelligently triggered by sensor data. The user may answer one or more questions with a touch screen on the faceplate device or via voice. An accelerometer and/or altimeter (e.g., based on movement) may register readings that indicate that a user has woken up for the morning. For example, ten minutes after the start of the consistent movements, the user may be presented with the question "How did you sleep last night?" As an additional, non-limiting example, though the regimen indicates that a glucose test is needed, the wrist-worn device may sense (via one or more sensors located on the monitoring device) that the user is currently taking a walk. As a result, the monitoring device may monitor for an opportunity to present the glucose test reminder (e.g., five minutes after sensor data indicates the user has sat down). At such time, the user may be presented with the reminder to activate a glucose test visually or textually. Thus, the regimen may be altered, or events may be delayed or indefinitely postponed based on sensor data.

In accordance with at least one aspect of the present disclosure, upon answering a question via the faceplate device, one or more sensors may be activated for a pre-determined period of time (e.g., 60 seconds). Such sensor data may be stored, or otherwise associated, with the answers to the question. The correlation or divergence of the data and answers can be useful in making the wellness index more robust. In some aspects, one or more sensors may be activated for a pre-determined period of time without first querying the wearer and receiving an answer via the faceplate device.

In accordance with at least one embodiment, the wellness index may be provided to the user via the monitoring device. In at least one example, the wellness index may be a numerical value in the range of 1-10. Additionally, or alternatively, the wellness index may be provided to a separate electronic device (e.g., a computer, a server). The wellness index may be used to display a graphical element (e.g., a colored dot) to the user indicating the patient's overall wellness. For example, a nurse responsible for caring for a number of patients may configure a medical provider device (e.g., a computer) to monitor a number of patient worn watches. The nurse's computer may receive wellness indexes for each patient and colored dots may appear on the user interface indicating overall wellness for each patient. In some cases, the colored dots may be overlaid on a graphical display of a ward floor plan or a map.

The wellness index can also be used to determine if the wearer is experiencing an emergency situation. In some aspects, a wellness index of 1-3 can indicate the wearer of the monitoring device is experiencing what can be classified as an emergency situation. In other aspects, a wellness index of 1-5 can indicate the wearer is experiencing an emergency situation.

In some aspects, the monitoring device can also include an emergency indicator that may be activated by the wearer to indicate the wearer is experiencing an emergency situation. For example, the monitoring device can include a button that is the emergency indicator and the device can be configured to detect when the button is pressed indicating the wearer is experiencing an emergency situation. In some aspects, the monitoring device can include a faceplate that acts as the emergency indicator. The monitoring device can be configured to detect when the faceplate is pressed and held for a pre-determined period of time. The monitoring device can also be configured to activate one or more sensors in response to detecting the activation of the emergency indicator to gather data related to the wellness of the wearer. In response to determining an emergency situation is affecting the wearer, the device can transmit an alert notification.

The monitoring device is configured with an antenna, receiver and transmitter, and is designed to communicate wirelessly on conventional cellular or data networks. When the monitoring device detects that an emergency situation is affecting the wearer, for example the wearer has fallen, the wellness index indicates an emergency situation, or the wearer activates an emergency indicator, it may generate and transmit an alert notification to medical facilities or an emergency dispatcher. The alert notification may include information about the wearer's location and elevation, as well as any other information relevant to assisting medical crews in locating and attending to the wearer. For example, health information that the wearer has previously inputted to the monitoring device or that has been generated by the sensors (e.g., heart rate, blood pressure, etc.) may be included in the alert notification transmitted in response to detection of the emergency situation or in a separate subsequent message.

The monitoring device can determine how to transmit the alert notification based on one or more factors, including the severity of the emergency affecting the wearer and the communication means available to the device at the time of the emergency. Consider the situation in which the monitoring device receives sensor data indicating the wearer's heart rate has stopped. The monitoring device determines that the wellness index of the wearer indicates an emergency situation is affecting the wearer and an alert notification should be sent to emergency personnel. The device determines that it is connected to a strong Wi-Fi connection and a weak cellular signal. In response to these determinations, the device can determine that the alert notification should be sent via the Wi-Fi connection. In an instance in which the device determines that the Wi-Fi connection is weak and the cellular signal is strong, the device can determine that the alert notification should be send via the cellular network.

In some aspects, for example when both the cellular network signal and Wi-Fi signal are weak, the monitoring device can determine to send the alert notification as an SMS or text message on the cellular network instead of a voice message or data message on either the cellular or Wi-Fi networks. The SMS message format can have a greater chance of a successful transmission on the weak cellular network than another message type on either the cellular or the Wi-Fi networks.

In some aspects, the monitoring device can determine the format of the alert notification (e.g., SMS or text message, MMS or data message, voice call, etc.) and the transmission method (e.g., via the Wi-Fi network or the cellular network). The monitoring device can determine the format and transmission method based type or severity of the emergency affecting the wearer and the availability of communication networks (e.g. signal strength of the networks). For example, in some aspects, the monitoring device can be configured to repeatedly send the alert notification. The monitoring device can cease transmission of the alert notification upon receiving confirmation of a successful transmission or receipt is received (e.g., from the cellular network). In other aspects, the monitoring device can continue to transmit the alert notification for a pre-determined period of time or a pre-determined number of transmission (e.g., 50 SMS message transmissions). In some embodiments, the monitoring device can determine a severity index for the emergency. The monitoring device can determine the severity index based on the wellness index of the wearer, a detection of a fall in combination with sensor or user profile data, or the detection of an activated emergency indicator in combination with sensor or user profile data.

In some aspects, the monitoring device can determine the format of the alert notification and method of transmission based, in part, on the battery (or power) level of the monitoring device. The algorithm used to determine the format of the alert notification and transmission method can include the battery level of the monitoring device as a factor. For example, it can require more battery power to make a voice call on the cellular or Wi-Fi networks than to transmit an SMS message on the cellular network. By transmitting the alert notification as an SMS message on the cellular network during a time of when the battery level of the monitoring device is below a pre-set level (e.g. 25% battery life) the monitoring device can increase the chances of transmission of the alert notification prior to the device losing battery power.

The monitoring device can also manage what sensors, functions, and/or transmissions are activated or performed based on the battery level of the monitoring device. For example, the monitoring device activate only select sensors that provide critical data related to the immediate wellness of the wearer (e.g., heart rate sensor) when the battery level of the monitoring device is below a pre-set value. In some aspects, the monitoring device can cease transmission of non-critical wellness data when the battery level of the device is below a pre-set value. For example, the monitoring device can continue to gather and store sensor data, responses to questions provided by the wearer, and other non-critical data related to wellness of the wearer, but refrain from transmitting that data off of the device when the battery level is below the pre-set value. Critical data, including, for example, a wellness index that indicates an emergency, activation of the emergency indicator, or a positive fall detection can continue to be transmitted away from the device, for example to emergency personnel. In other aspects, an algorithm can determine which sensors and what monitoring functionality is performed by the monitoring device based on information, including heath data related to the wearer, the battery level, the current wellness index of the wearer, or other information available to the monitoring device.

Several technical features of the monitoring device will now be described with respect to the accompanying drawings.

Referring now to the drawings, in which like reference numerals represent like parts, FIG. 1A depicts an example environment 100 of an embodiment of a wrist-worn device 108 for monitoring the health or wellness of a user or wearer of the wrist-worn device 108. The wrist-worn device 108 can include a wellness monitoring engine, an emergency detection engine, a fall detection module (or engine), and other engines described herein. In accordance with at least one embodiment, a medical provider 107 (e.g., a physician, nurse, or a pharmacist) configures the wrist-worn device 108 with a prescribed therapy. The wrist-worn device may include a wristband monitoring device 110 and a faceplate device 112. The medical provider 107 uses a medical provider device 106 (e.g., a laptop, desktop, iPad®, tablet) to input information associated with the therapy. Upon receipt, the information associated with the therapy is received by the wellness monitoring engine. Once received, a regimen is determined for the therapy. The wrist-worn device 108 utilizes one or more sensors to monitor the patient's vital signs according to the regimen. The wrist-worn device 108 enables interaction between the wellness monitoring engine, the emergency detection engine, the fall detection module, and the user. The wrist-worn device 108 may be used to illicit affirmative user input, to display information to the user, to wirelessly transmit patient data to service provider computers 116, and to receive information or data from service provider computers 116. A wellness index representing a patient's overall wellness, may be determined by wellness monitoring engine using data collected by the sensors, information received from the user, and/or additional information or data.

Service provider computers 116 includes one or more computing devices responsible for storing and/or managing medical-related data associated with the patient. Service provider computers 116 may communicate wirelessly with a wellness monitoring engine to provide information regarding the therapy via a network 114. This information includes therapy configuration. Additionally, as described above, the medical provider 107 can utilize the medical provider device 106 to modify a therapy. Such modifications are communicated to service provider computers 116 via the network 114. Service provider computers 116 records such modifications and communicates the modifications to wellness monitoring engine.

In some embodiments network 114 is a cellular network. Wrist-worn device 108 may exchange cellular network control, timing and status information with a cellular network access point so as to maintain communication capabilities in the cellular network. Cellular network access points may provide access to the internet or other data networks. The wrist-worn device 108 may establish an internet connection by detecting a cellular access point, performing joining procedures, and regularly exchanging status, control and routing information with the access point. The wrist-worn device 108 is also in communication with SPS satellites 117 for determining the location of the wrist-worn device 108. The wrist-worn device 108 may use the internet connection to access weather data, additional GPS data (e.g. maps), or to communicate with other devices described herein. In some aspects, the wrist-worn device 108 accesses most recently available barometric pressure information, which it uses to adjust the elevation measurements provided by its altimeter, so as to correct for changes in atmospheric pressure.

The wrist-worn device 108 receives GPS information transmitted by SPS satellites 117 and land-based communication platforms in one embodiment. A GPS component of the wrist-worn device 108 uses this information to periodically determine a latitude and longitude that represent the monitoring device position. The wrist-worn device 108 uses this location information for any of several different purposes. For example, when the wrist-worn device 108 accesses a data network 114 to obtain current weather information, the wrist-worn device 108 uses the location information to identify a nearest weather station or observation locale from which to retrieve current barometric pressure data.

The wrist-worn device 108 uses location information as an additional means of confirmatory data for avoiding false positive fall detections when data from other sensors is consistent with a fall having occurred. For example, when changes in acceleration or altitude data is indicative of a fall, location information may be used to determine that the wearer is actually mobile, and that the change in the altitude or acceleration data is actually a false indication. Such a scenario may occur, for example, when the user is in an accelerating vehicle travelling down a hill. In such a hypothetical case, downwards acceleration of the vehicle might be similar to the typical acceleration data registered when a fall occurs. However, the movement of the vehicle, as registered by changing GPS data, would reveal that the wearer is in motion and therefore has not fallen on the ground.

Figure 1B:
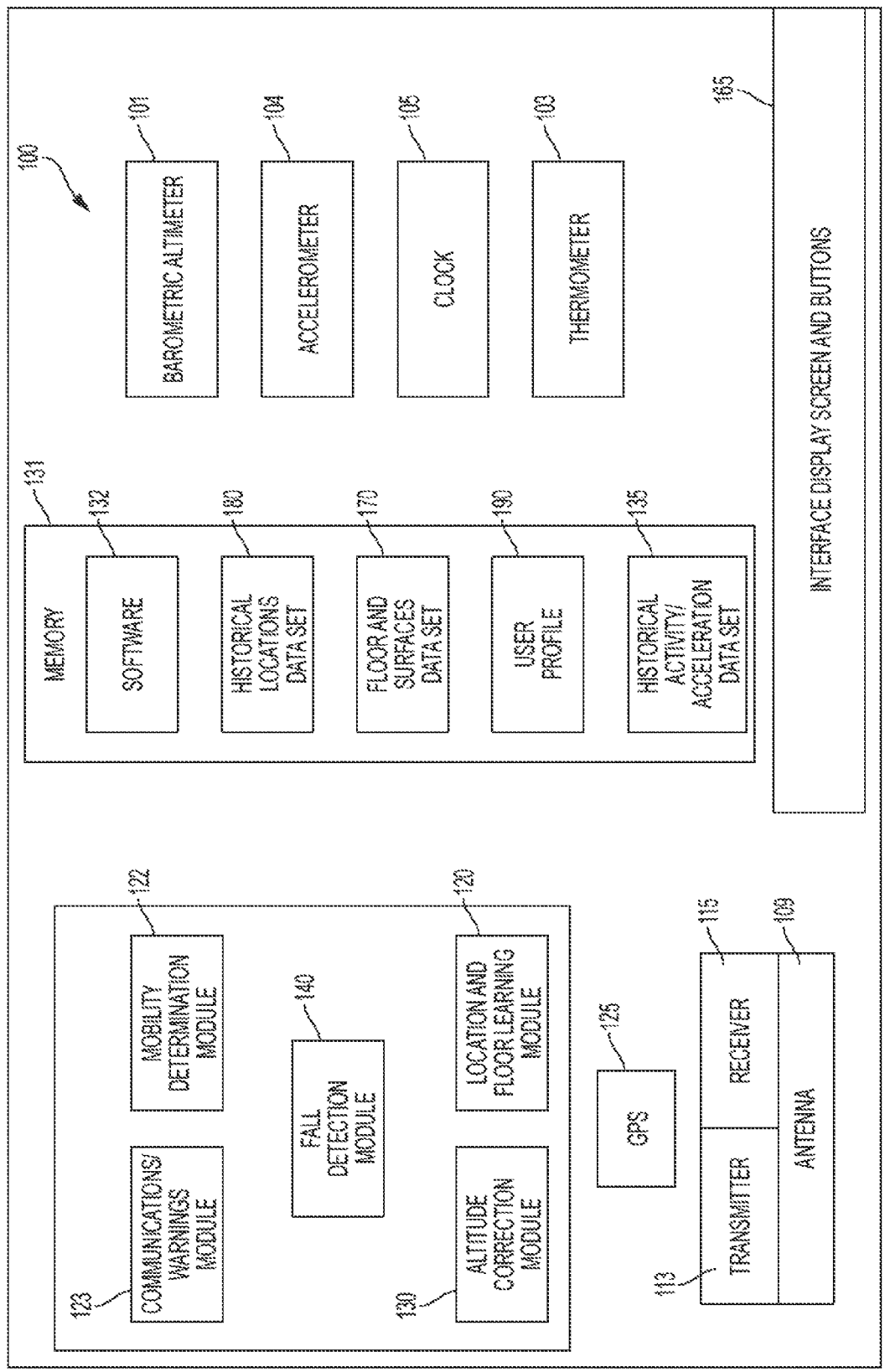
FIG. 1B illustrates example components of the fall detection device of the present disclosure.

The wrist-worn device 108 also uses location information to learn the latitude and longitude of buildings in which the wearer spends significant time, and sense that it is present within a building. The wrist-worn device 108 uses a building sensory capability within the broader learning process used to determine the elevations of floors and surfaces within a building. FIG. 1B provides a simplified and generalized diagram of example components and modules of the wrist-worn device 108, including certain simplified components for detecting falls using the techniques and processes described herein. FIG. 1B illustrates that the wrist-worn device 108, as mentioned previously, includes a barometric altimeter 101, GPS 125, thermometer 103, accelerometer 104, clock 105 and user interface 165. The barometric altimeter 101 includes a transducer configured to generate an analog voltage signal that varies in proportion to changes in atmospheric pressure impinging on the transducer.

A control component within the altimeter 101 is used to receive a control signal from the altitude correction module 130 of processor 121. The control signal is used to bias or trim the voltage signal in a manner that compensates for the changes in sensed pressure caused by climatic changes. The altitude correction module 130 generates the control signal based on the most recent weather information received by the wrist-worn device 108. An analog to digital converter (not shown) at the altimeter output is used to provide periodic digital elevation data.

The fall detection module 140 analyzes acceleration, elevation, temperature and GPS data to detect and confirm falls. The fall detection module 140 uses elevation data as primary data for detecting a fall. That is, the fall detection module 140 analyzes elevation observations as they are obtained, and in conjunction with preceding observations, to determine if the observations are consistent with a fall. This use is in contrast to use of elevation data as confirmatory data. When a type of data is confirmatory data, observations are only analyzed for fall detection purposes when they coincide with a determination, based on other data, that a fall may have taken place.

Depending on the performance characteristics of the accelerometer 104 and the altimeter 101, acceleration data may be more suitable than elevation data for use as primary data in detecting falls. In this case, use elevation data as confirmatory data may facilitate computational efficiency and enable lower power consumption within the wrist-worn device 108.

The thermometer 103 provides digital temperature data that is also used as a source of confirmatory information when acceleration data and elevation data is consistent with a fall. The temperature data provides a means for determining that the wearer has removed the wrist-worn device 108. This capability is important for preventing false-positive fall detections because removing the wrist-worn device 108 and placing it on a small table or nightstand may result in acceleration and altimeter data that is similar to the data produced during a fall.

In general, when the wrist-worn device 108 is removed from the wearer's body, the temperature data declines quickly and steadily towards room temperature. Moreover, when a wearer falls, the temperature data normally increases slightly. By detecting a steadily falling temperature, the wrist-worn device 108 avoids false-positive fall detections caused by the wrist-worn device 108 being removed from the body.

The wrist-worn device 108 is equipped with data processing capabilities and learning features that enable it to sense when it is within a building (or other area that the wearer frequents and which is flat, such as a backyard), identify the building and learn the elevations of floors and other surfaces therein. The processing associated with these detection and learning features is controlled by the location and floor learning module 120 of processor 121. The processing involved in sensing that the wrist-worn device 108 is within a building includes analysis of GPS data and time data using procedures that will be described more thoroughly in subsequent paragraphs. Analysis of elevation data is also be used as part of this sensing process.

When the wrist-worn device 108 detects that it has been brought into a building that has not previously been detected, the location and floor learning module 120 causes the building location to be stored in the historical locations data set 180. Additionally, when presence within a building is sensed (whether a previously detected or unknown building), the locations and floor learning module 120 causes the wrist-worn device 108 to enter a data gathering and analysis mode that will be referred to hereinafter as the elevation learning mode. While the elevation learning mode is active, the locations and floor learning module 120 causes GPS, elevation, time and temperature information to be temporarily stored as time series data. This information is stored in the floor and surfaces data set 170, and is indexed to the building location. The locations and floor learning module 120 periodically analyzes the data to learn the elevations of surfaces and floors in the building.

When a floor or surface elevation is learned, the locations and floor learning module 120 stores the information about the elevation in the floor and surfaces data set 170. For example, the stored information indicates the elevation determination, the building in which the elevation was learned, and whether the elevation corresponds to a surface or a floor. Elevation information stored in this way is incrementally refined through later analysis, and is used by the fall detection module 140 when confirmation or rejection of a fall hypothesis is needed.

Furthermore, while the wrist-worn device 108 is in the elevation learning mode, the locations and floor learning module 120 continues to analyze GPS data for the purposes of detecting removal of the wrist-worn device 108 from the building. When the wrist-worn device 108 is determined to have been removed from the building, the elevation learning mode may be suspended and the locations and floor learning module 120 then analyzes GPS data to detect entry into other buildings.

The location and floor learning module 120 manages the processing associated with detecting presence within buildings, storing building locations and learning elevations of surfaces and floors in the building. The location and floor learning module 120 may be designed so as to catalog and learn elevations with respect to buildings in which the wearer spends a significant portion of time.

The location and floor learning module 120 uses several different techniques to learn building locations and detect when a user is in a known building. One method for learning building locations involves detecting loss of GPS 125 service followed, after a substantial delay, by reestablishment of service close to where the service interruption occurred.

Commonly, the quality of signals transmitted by satellites is impeded by the walls and enclosures of buildings. Thus, GPS 125 position information is oftentimes unavailable when a GPS 125 device is brought within a building, and lost GPS 125 information is frequently caused by entering a building. Similarly, reestablishment of GPS service frequently occurs when a wearer exits a building in which GPS 125 service was unavailable. For this reason, the location and floor learning module 120 determines where and when GPS 125 service is lost and regained in order to detect and determine the location of a building that the monitoring device has not previously detected.

However, certain buildings and homes do not interfere with the reception of GPS data. For this reason, the location and floor learning module 120 uses an additional method for building identification that is based on detection of long periods of unchanged GPS 125 location data. As part of this methodology, a threshold number of such detections at any one location or a minimum frequency of detections during a prescribed time period is used as a condition for determining that a building exists at that location. Such conditions are used to prevent the wrist-worn device 108 from performing operations to learn elevations of floors and surfaces in buildings which the wearer does not routinely visit.

While performing analysis of GPS data to detect new buildings, the location and floor learning module 120 may also compare each incremental GPS location to determine if the most recent GPS location coincides with the location of a building entry in the buildings data set. When a GPS locations coincide with the location of a building entry, the location and floor learning module 120 activates the elevation learning mode.

The location and floor learning module 120 further incorporates a feature for determining that all of the buildings most frequently visited by the wearer have been detected. When this determination feature is used, the processing associated with learning new building locations is terminated or temporarily halted upon the determination being made. In this way, the wrist-worn device 108 conserves processing resources which otherwise might be devoted to learning the locations of buildings which the wearer rarely visits and are therefore unlikely to be the location of a fall.

The wrist-worn device 108 also includes a transmitter 113, receiver 115 and antenna 109. The transmitter 113 and antenna 109 facilitate emergency communication of fall alert messages and other relevant monitoring or wearer information. The emergency communications are transmitted on any wireless network such as a cellular network, data network or satellite network. The receiver 115 and antenna 109 facilitate receiving communications associated with alert messages, as well as software updates and other information used at the wrist-worn device 108. The receiver 115 is also used to receive weather information from a data network, and provide the weather information to the altitude correction module 130.

The processor 121 executes software 132 or other instructions stored in memory 131. The software 132 controls the gathering, recording, analysis, organization and storage of sensor data and user inputted data. When the processor 121 executes the software 132, the software 132 causes several processing modules to become active within the processor 121. The processor modules include a mobility determination module 122, a communications/warnings module 123, the fall detection module 140, a the location and floor learning module 120, and the altitude correction module 130.

The altitude correction module 130 performs operations and schedules data network communications to periodically obtain weather data for the area in which the wrist-worn device 108 is being operated. The altitude correction module 130 uses this data to determine an altitude correction factor to account for atmospheric pressure variations affecting the pressure sensed by the altimeter 101. The altitude correction module 130 then generates a control signal that is proportional to the altitude correction factor. The altitude correction module 130 provides the control signal to a control component (not shown) within the barometric altimeter 101. The control component adjusts the analog to digital conversion process that yields the outputted digital elevation data so that the output will reflect only actual elevation change and will not reflect pressure changes resulting from climatic variation.

The altitude correction module 130 receives and monitors GPS 125 data to detect changes in the location of the wearer. For so long as the wearer's location remains relatively constant, the altitude correction module 130 obtains regularly scheduled weather information updates. The weather information updates are transmitted by a remote server to the wrist-worn device 108 over the data network. The wrist-worn device 108 reports its geographic location to the server so that the server may select weather information corresponding to the location of the wrist-worn device 108. Alternatively, relevant weather information is provided based on the location of a base station, relay station, or other network access point from which the wrist-worn device 108 receives network data. In either of these cases, the regularly scheduled weather updates may be obtained in much the same way that weather information is received at a mobile device or smartphone that executes application software for displaying recent weather data.

The altitude correction module 130 is also designed with functionality for soliciting a weather update at an unscheduled time. Soliciting a weather update in this manner may be beneficial when the position of the wrist-worn device 108 has changed substantially in a short amount of time. Soliciting a weather update is performed by using the data network to send a weather update request signal to the remote server.

The accelerometer 104 may be a digital device capable of repeatedly generating digital acceleration data at a fixed measurement tine interval. The fall detection module 140 repeatedly analyzes a window containing a fixed number of most recent acceleration observations, and determines whether the analyzed data satisfy a sufficient or threshold number of fall conditions for a fall possibility hypothesis to be generated. The window may be updated at a fixed interval so as to reflect newly registered data, and the data in the window may be analyzed each time the window is updated. For example, the window may be updated and reanalyzed each time a new altitude data observation is registered, or may be updated and reanalyzed at any other fixed interval of time.

Hereinafter, this window will be referred to as an acceleration analysis window. The fall detection module 140 described and covered by this disclosure is configured to analyze the acceleration analysis window and determine if the data in the analysis window satisfies any number or combination of fall conditions, and this description is not intended to be limited to wearable fall detection devices using certain specific fall conditions or combinations thereof.

A simple example of a fall condition is a threshold acceleration condition that is satisfied when a minimum number of data observations in the analysis window represent downwards or upwards acceleration in excess of a threshold chosen based on the characteristics of falls analyzed in a testing environment. Similarly, an acceleration range condition may be used. An acceleration range condition is a condition defined so as to be satisfied when some specified number of data observations in the analysis window represent downwards or upwards acceleration within a specified acceleration range. The acceleration range may be defined based on the characteristics of falls analyzed in a testing environment.

Another condition that will be explained in subsequent paragraphs is satisfied when the acceleration data in the analysis window is similar to a modeled fall (hereinafter referred to as a "fall profile"), as represented by a series of hypothetical acceleration observations. To determine if this condition is satisfied, the fall detection module 140 performs point by point comparisons of the acceleration data in the analysis window and the hypothetical acceleration observations provided by the model. Each point by point comparison yields a difference, and the fall detection module 140 sums the differences yielded by the comparisons of the various data points in the observation window. The sum is considered to represent what will be referred to hereinafter as a deviation from the fall profile.

If the deviation is less than a threshold amount, the fall detection module 140 determines the condition to be satisfied. The fall profile and the threshold amount is encoded into the software 182. These parameters may be determined in a testing environment by comparing the fall profile to data obtained during actual falls, and determining a distribution of the deviations registered in these studied cases. Based on the distribution of deviations, the threshold is set so as to achieve a desired balance between the detection of actual falls on one hand, and the avoidance of false-positive detections on the other hand.

The fall detection module 140 is designed to use any number of other such conditions relevant to detecting a fall based on acceleration data, regardless of the simplicity or complexity of the conditions. The fall detection module 140 generates a fall possibility hypothesis upon certain combinations of conditions being satisfied, upon a threshold number of conditions being satisfied, or upon any single condition is satisfied. When the fall detection module 140 makes such a hypothesis, it subsequently analyzes elevation, temperature and GPS data for the purpose of confirming that a fall occurred.

In certain implementations of the techniques described herein, the fall detection module 140 may be designed so as to determine that a fall has occurred when analysis of the elevation data confirms the fall possibility hypothesis. Alternatively, in other implementations, the fall detection module 140 is configured to make such a determination only when temperature and/or GPS data do not contradict the fall hypothesis, or confirmation is provided by some combination of the elevation, GPS and temperature data.

As will be described in later paragraphs, the wrist-worn device 108 fall detection module 140 senses that recent acceleration data is consistent with a fall based on comparing the acceleration data in the acceleration analysis window to a fall profile. The fall profile is an acceleration model representing an expectation of the acceleration data that would be observed upon a fall occurring. For example, a fall profile may be a discrete function showing the magnitude and duration of expected downwards acceleration, and a magnitude and duration of acceleration in the upwards direction. The expected acceleration in the upwards direction is the acceleration expected to result from a wearer breaking the fall with his hands.

A fall profile is represented by a series of hypothetical acceleration data points, such that the number of data points is commensurate with the number of actual acceleration data points considered in each instance of the acceleration analysis window. A fall profile is deduced or established in a development phase, through use of any one of several methodologies. For example, in the development phase, accelerometers may be used to study actual falls suffered by a variety of people for which characteristics such as height, weight, age mobility and activity level are known. This acceleration data may be studied for different groups of similarly characterized users, and an average fall profile may be calculated mathematically for each such user group.

Humans who are highly mobile and active tend to accelerate differently when suffering a fall, as compared to other humans who are less active. People who are mobile and active tend to suffer falls associated with tripping or slipping, while those who are inactive tend to suffer falls associated with collapsing, feinting or losing the necessary strength to sustain themselves. Falls caused by slipping or tripping tend to occur faster, and with greater acceleration than falls caused by collapsing feinting or losing strength.

Similarly, tall people fall differently from shorter individuals. For example, on average, a fall suffered by a tall person will involve greater acceleration than a fall suffered by a short person, and may be punctured by sharper deceleration (upwards acceleration) when the fall is broken. For this reason, the software 132 provides the wrist-worn device 108 with several different fall profiles, each of which is intended for use in association with a specific combination of wearer mobility and height characteristics.

Figure 2B:
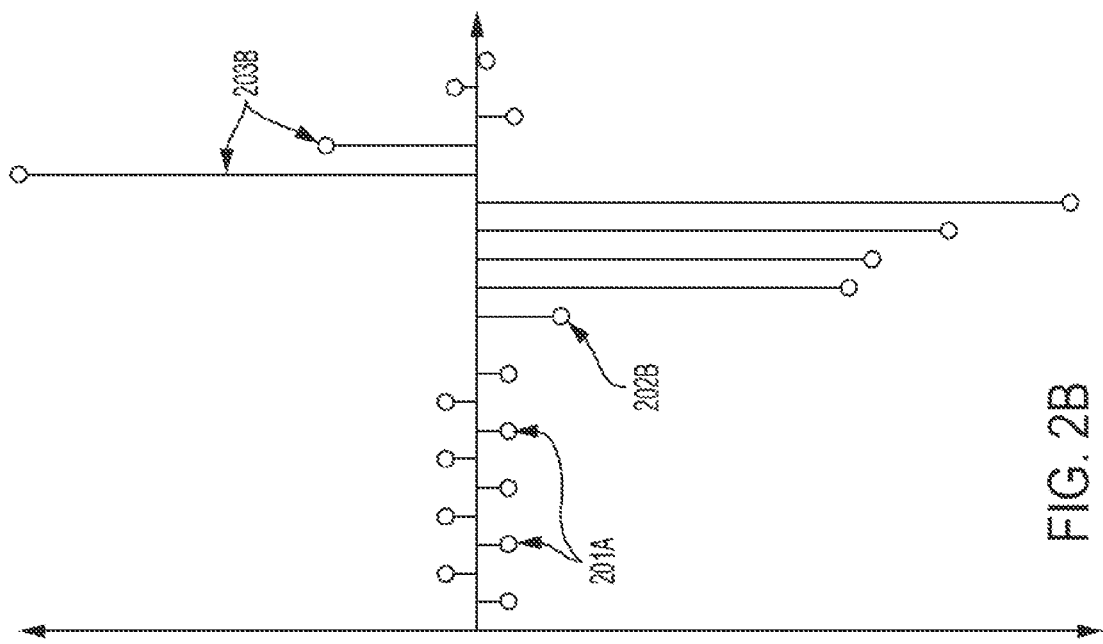
FIGS. 2A and 2B illustrate example fall profiles with respect to a shorter wearer and a taller wearer, respectively.
Figure 2A:
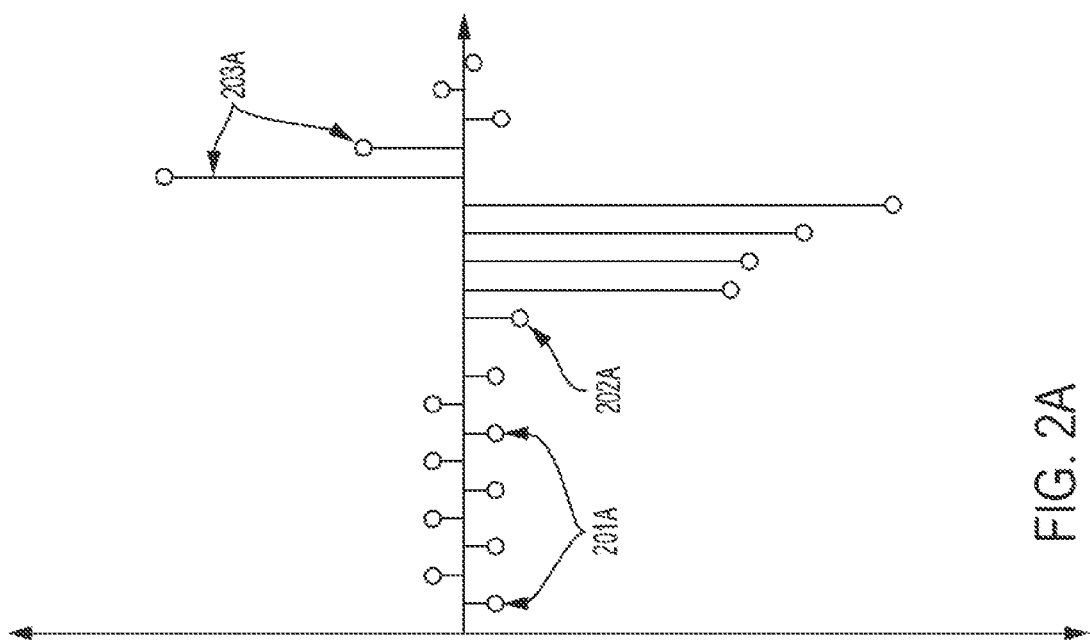

FIG. 2A and FIG. 2B show two examples of hypothetical fall profiles, 2A, 2B. FIGS. 2A and 2B are intended to comparatively show how the fall detection module 140 uses a fall profile that is customized in view of the wearer's height, as learned from wearer information which the wrist-worn device 108 may solicit and store in user profile 190, and which may be inputted through the user interface 165. It should be understood that FIGS. 2A and 2B are highly simplified, and are presented so as to explain general concepts only. In actuality, a functional fall profile may need to contain many more acceleration data points, and the relative magnitudes of consecutive data points may be substantially different than the FIGS. 2A and 2B might seem to imply.

FIGS. 2A and 2B are intended to show how a fall detection profile used to monitor the condition of a short wearer is different from a fall detection profile used to monitor the condition of a taller user. For example, as compared to the fall profile in FIG. 2B, the fall profile in 2A is more accurate when applied to monitor the well-being of a short user, and fall profile 2B may be understood as a profile that could hypothetically be more suitable to monitoring a taller user.

As depicted in FIGS. 2A and 2B, each fall profile includes several consecutive acceleration data points shown in time series, such that every two consecutive points are spaced 200 milliseconds apart. The expected acceleration data points of a fall profile are given with respect to a periodic time interval that is equivalent to the measurement interval of the accelerometer in the monitoring device.

Moreover, at 201A and 201B, the fall profile includes acceleration data points that indicate a relatively small amount of vertical acceleration, as ordinarily occurs when a wearer is sitting down, standing still, or walking at a normal speed. A first data point associated with initiation of a fall is shown at 202A and 202B. Both FIGS. 2A and 2B show how acceleration is expected to increase as a fall develops. This expectation is manifested in the several consecutive data points occurring after 202A, 202B, each of which shows steadily increasing acceleration in the downwards direction. However, in FIG. 2B, these several consecutive data points have greater magnitude than the corresponding data points of FIG. 2A. This difference is a result of the fact that taller individuals tend to fall with greater acceleration than shorter individuals.

In FIGS. 2A and 2B, the depicted fall profiles include data points representing an expected upwards acceleration caused by fall breakage associated with hitting the ground backwards or impacting the ground hands first. As compared to a short wearer, a tall wearer will commonly fall with higher vertical acceleration. Thus, the upwards acceleration occurring upon a fall being broken will ordinarily be higher as well. For this reason, fall profile data points 203A show a larger expected magnitude of upwards acceleration than data points 203B.

The mobility determination module 122 includes instructions for enabling the wrist-worn device 108 to determine information about the wearer's lifestyle so that a fall profile that is customized to the wearer's height can be further customized to the wearer's level of activity (e.g. often the wearer is standing or walking) and mobility (e.g. how fast the wearer moves). The wearer activity and mobility may be determined by soliciting the wearer's personal assessment of these characteristics by way of the interface 165 functionality, as controlled by the communications/warnings module 123. When activity and mobility information is obtained or updated, it may be stored in the user profile 190 and used at any time as a reference for customizing a fall profile for the wearer.

In addition to soliciting activity and mobility information from a wearer, the mobility determination module 122 may determine the wearer's activity and mobility by analyzing recent GPS data, acceleration data and elevation data. As this data is generated, it may be stored in the activity/acceleration dataset 135 for future analysis by the mobility determination module 122. The data may be stored in a manner that is suitable in view of the processing configuration and depth of the analysis used by the mobility determination module 122. However, the data analyzed by the mobility determination module 122 should be filtered so that the module does not consider rapidly changing data of the sort that could result only from the user being propelled by a car, airplane, or other means beyond the wearer's own physical efforts.

Once rapidly changing data is eliminated by filtering, the remaining GPS, acceleration and altimeter data may be stored chronologically in respective data structures within the historical activity/acceleration data set 135. Moreover, each data observation may be indexed to a time stamp indicating the time at which the observation was registered. The mobility determination module 122 may periodically calculate metrics representative of the mobility of the wearer by processing recently stored data in the historical activity/acceleration dataset 135. For example, the mobility determination module 122 may analyze this data on a daily or weekly basis and calculate an average amount of time that the wearer spent moving, and the wearer's average speed when moving. The mobility determination module 122 may use these calculations to categorize the user as either mobile or immobile, and active or inactive, or may make more granular characterizations in this regards.

The fall detection module 140 periodically references the most recent activity and mobility characterizations made by the mobility determination module 122. The fall detection module 140 uses the characterizations as a basis for selecting from memory and activating a fall profile that is appropriate in view of the wearer's physique, mobility and activity. The selected fall profile is then used by the fall detection module 140.

Figure 3B:
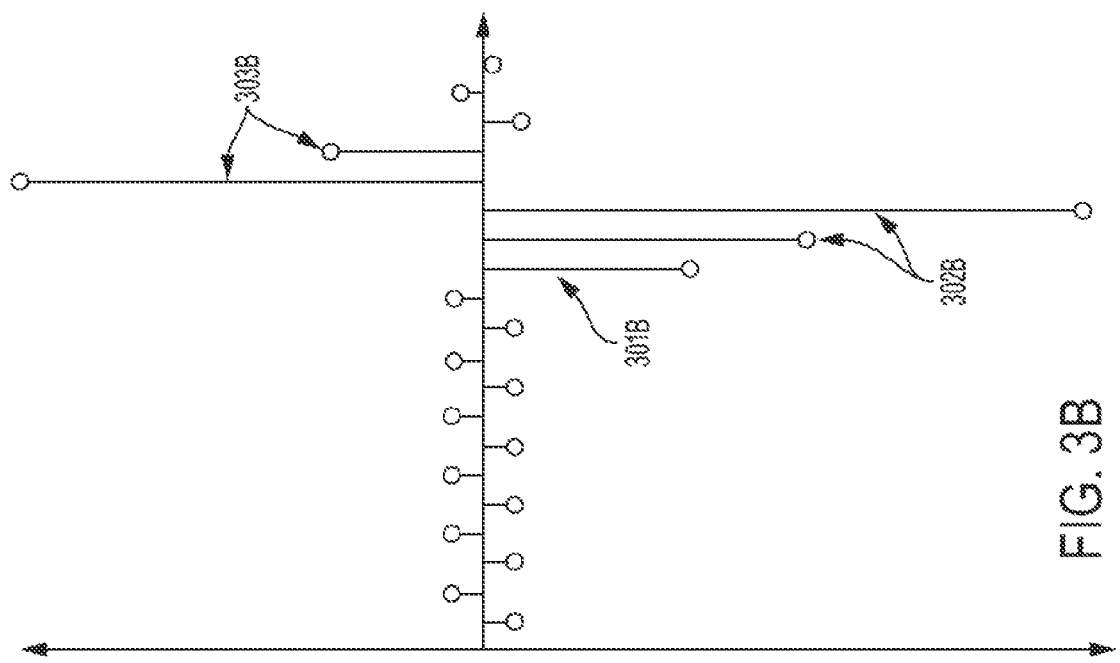
FIGS. 3A and 3B illustrate example fall profiles with respect to a relatively inactive and immobile wearer and a relatively more active and mobile wearer.
Figure 3A:
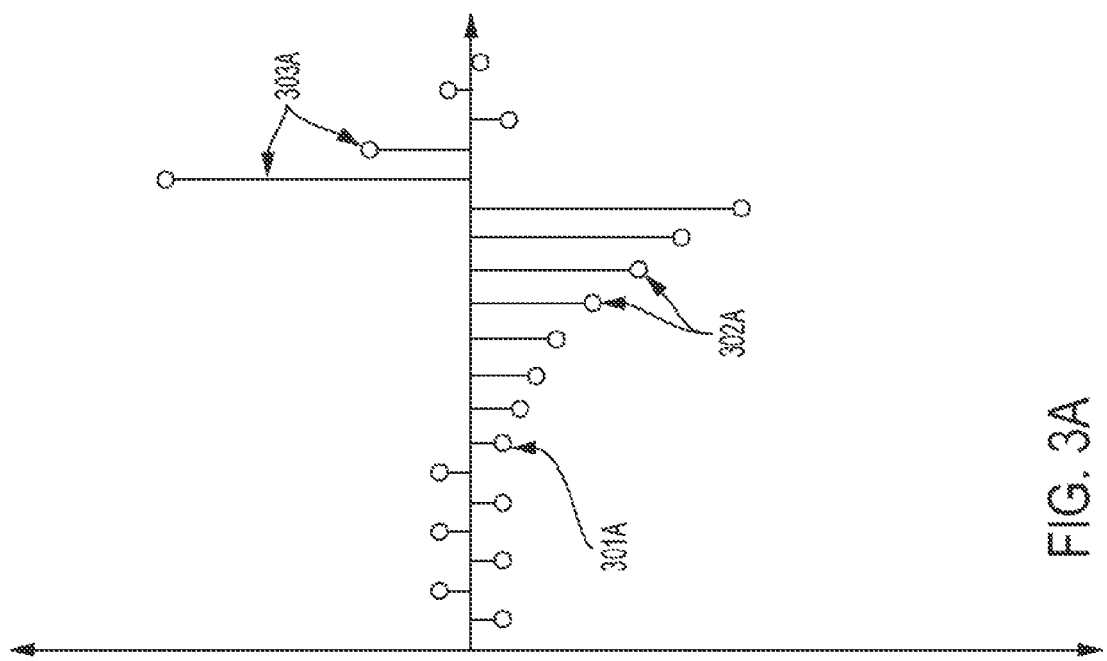

FIG. 3A and FIG. 3B show two examples of hypothetical fall profiles, 3A, 3B. FIGS. 3A and 3B are intended to show, by way of a comparison, how the fall detection module 140 may use a fall profile that is customized in view of the wearer's activity and mobility. For example, FIGS. 3A and 3B are intended to show how a fall profile used in monitoring the condition of an inactive and immobile wearer may be different from a fall profile used in monitoring the condition of a wearer who is mobile and active. For example, as compared to the fall profile in FIG. 3A, the fall profile in 3B may be more accurate when applied to monitor the well-being of a more active and mobile user, and fall profile 3A may be understood as a profile that could hypothetically be more suitable to monitoring a user who is less active and mobile.

As depicted in FIGS. 3A and 3B, each fall profile includes several consecutive acceleration data points, such that every two consecutive points are spaced 200 milliseconds apart. The expected acceleration data points of a fall profile are given with respect to a periodic time interval that is equivalent to the measurement interval of the accelerometer 104 component.

A first data point associated with initiation of a fall is shown at 301A and 301B. Both FIGS. 3A and 3B show how acceleration is expected to increase as a fall develops. This expectation is manifested in consecutive data points 302A, 302B, each of which shows steadily increasing acceleration in the downwards direction. However, in FIG. 3B, the acceleration increases more rapidly, and the data points show greater magnitude than the corresponding data points of FIG. 3A. Also, the profile of the fall modeled in FIG. 3B occurs in a smaller amount of time than the profile of the fall modeled in FIG. 3A.

Figure 4:
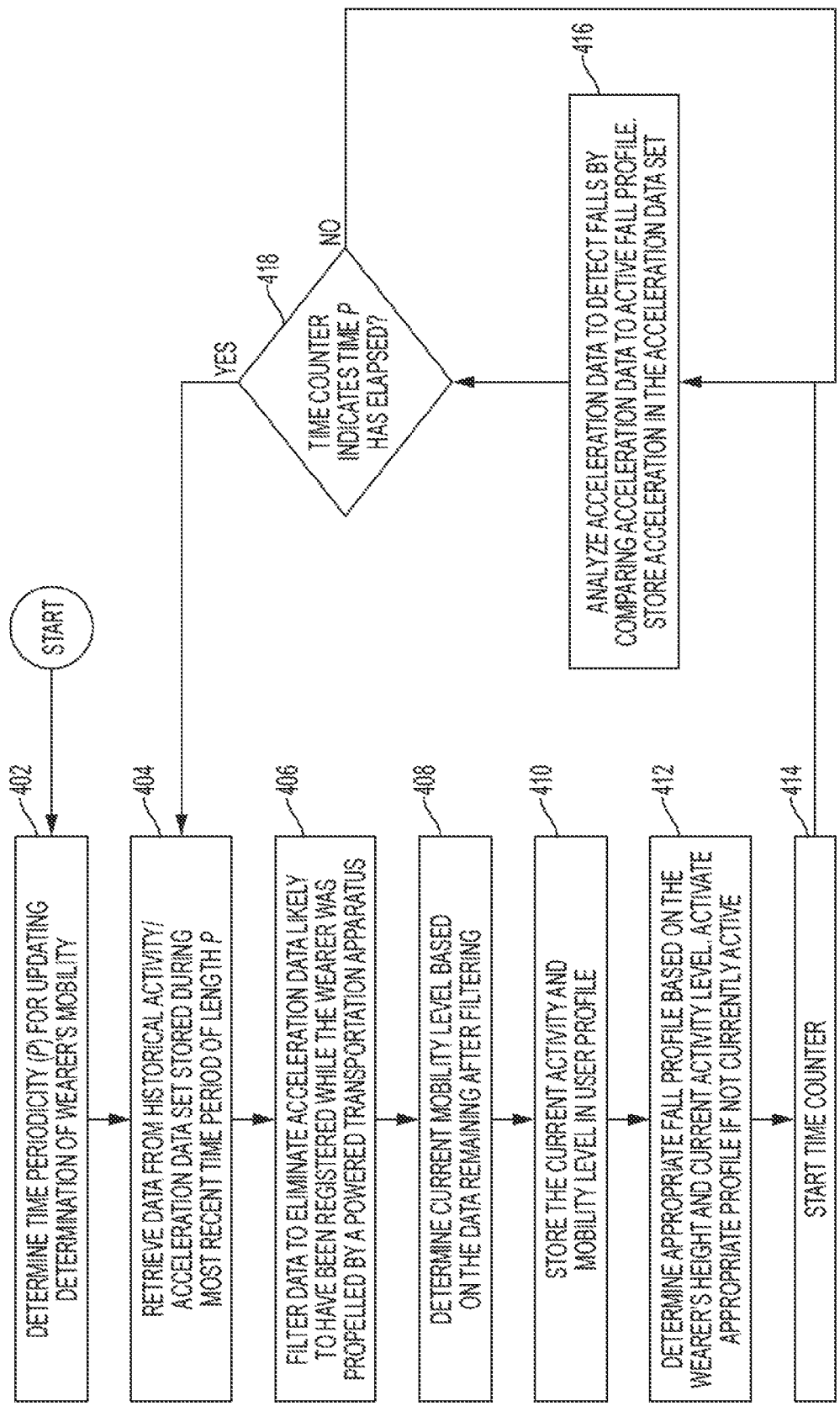
FIG. 4 is a flow chart illustrating example operations for determining a wearer's mobility and activity level.

FIG. 4 is an embodiment of a flowchart that provides example operations performed by the mobility determination module 122 to determine and update a wearer's level of activity and mobility so that a suitable fall profile is used for fall detection purposes. The operations begin at 402, and involve the mobility determination module 122 first retrieving a time periodicity parameter that dictates the period of the cycle to be used for updating the wearer's activity and mobility. At 404, the mobility determination module 122 retrieves data from the historical activity/acceleration data set 135. The retrieved data is recent acceleration, GPS or elevation observations stored since the last occasion on which the wearer's mobility and activity level was determined.

At 406, the mobility determination module 122 filters the retrieved data to eliminate elevation, GPS or acceleration data likely to have been registered while the wearer was propelled by a power transportation apparatus. As mentioned previously, this filtering is performed so that only data representing the wearer's own physical efforts will be evaluated in determining the activity and mobility. At 408 the mobility determination module 122 estimates the wearer's current mobility and activity level based on the data remaining after the filtering described at 406. At 410, the mobility determination module 122 stores the determined mobility and activity levels in the wearer's profile.

At 412, the mobility determination module 122 determines an appropriate fall profile based on the wearer's height and current mobility and activity levels, as estimated at 406. This fall profile is then provided to the fall detection module, which activates it.

At 414, the mobility determination module 122 starts a time counter that it uses to determine when the wearer's mobility and activity should be next updated. At 416, the fall detection module 140 analyzes acceleration data to detect falls. The fall detection module 140 performs this analysis by comparing acceleration data to the most recently activated fall profile. At 418, the mobility determination module 122 determines whether the counter indicates that time p has elapsed since the counter was started at 412. If the counter does not so indicate, then the fall detection module 140 continues to use the active fall profile to detect falls. The use of the active fall profile is continued until the counter indicates that time p has elapsed, at which time a new activity and mobility determination is made, beginning with the retrieval of acceleration data specified at 404.

The wrist-worn device 108 of the present disclosure may include features for communicating with the wearer to determine the wearer's condition when a fall is detected. For example, when sensor data is indicative of a fall and the analysis performed by the fall detection module 140 indicates that a fall likely occurred, the communications/warnings module 123 may generate a message and prompt on the user interface (e.g., a display screen) 165. The message and prompt may be accompanied by a distracting sound for attracting the wearer's attention. Upon issuing the message and prompt, the communications/warnings module 123 may initiate a countdown clock.

The message serves to inform the wearer that the wrist-worn device 108 has detected the possibility of a fall and enables a wearer who has not fallen to indicate this fact. If such an input is not received by the time the countdown clock has expired, the wrist-worn device 108 transmits communications to a dispatch or emergency response service.

The wrist-worn device 108 is designed to operate in a mode in which the transmission of an alert is prevented by an input indicating that a fall has not occurred. In such a case, the wrist-worn device 108 resumes monitoring the user in the same manner as before the possibility of a fall was detected.

The wrist-worn device 108 also incorporates a further mode of operation in which a countdown timer is initiated upon receiving an input from a wearer indicating that a fall has not occurred. In this mode, the fall detection module 140 analyzes GPS, elevation and acceleration data for an indication of user movement. If the GPS, altitude and acceleration data are consistent with the wearer lying on the ground throughout the period during which the countdown clock is active, the wrist-worn device 108 solicits a second request for information from the wearer. On this occasion, if the wearer's input indicates that a fall has occurred, the wrist-worn device 108 then transmits an alert to dispatch or emergency services. The alert includes GPS information that represents the wearer's location, as well as elevation data so that, in case the wearer is in a tall building, emergency personnel can determine the floor on which the wearer is located.

The premise underlying this second mode of operation is that individuals may be in shock upon falling, or may initially be ashamed or hesitant to admit that they need help. In such cases, the second solicitation for information from the wearer serves to enable confirmation of the fall after the wearer's shock has subsided or after the wearer has recognized that help is necessary.

The device may also include an emergency communications feature that enables the wearer to trigger communications to a dispatch or emergency response service, regardless of whether a fall is detected by the wrist-worn device 108. For example, the wrist-worn device 108 may be designed so that this emergency communications feature can be activated by touching or pressing down on the user interface (e.g. a display screen) 165 for a threshold time duration.

The user interface 165 may provide an interface with functionality for reprogramming, calibrating or setting the wrist-worn device 108 in any number of ways. However, because such interfaces may be confusing, distracting or problematic for certain wearers, this control functionality may be hidden, so that it is only made apparent and accessible when a specific code or input has been provided. For example, the wrist-worn device 108 may be configured so that the control functionality is displayed only after the user interface (e.g., display screen) 165 has been touched, pressed, or tapped in a certain way.

At all other times, the screen shows a standard watch display, including the time of day. The wrist-worn device 108 may count strides taken by the wearer, and display this information on the user interface (e.g., display screen) 165, in combination with the time.

Figure 5:
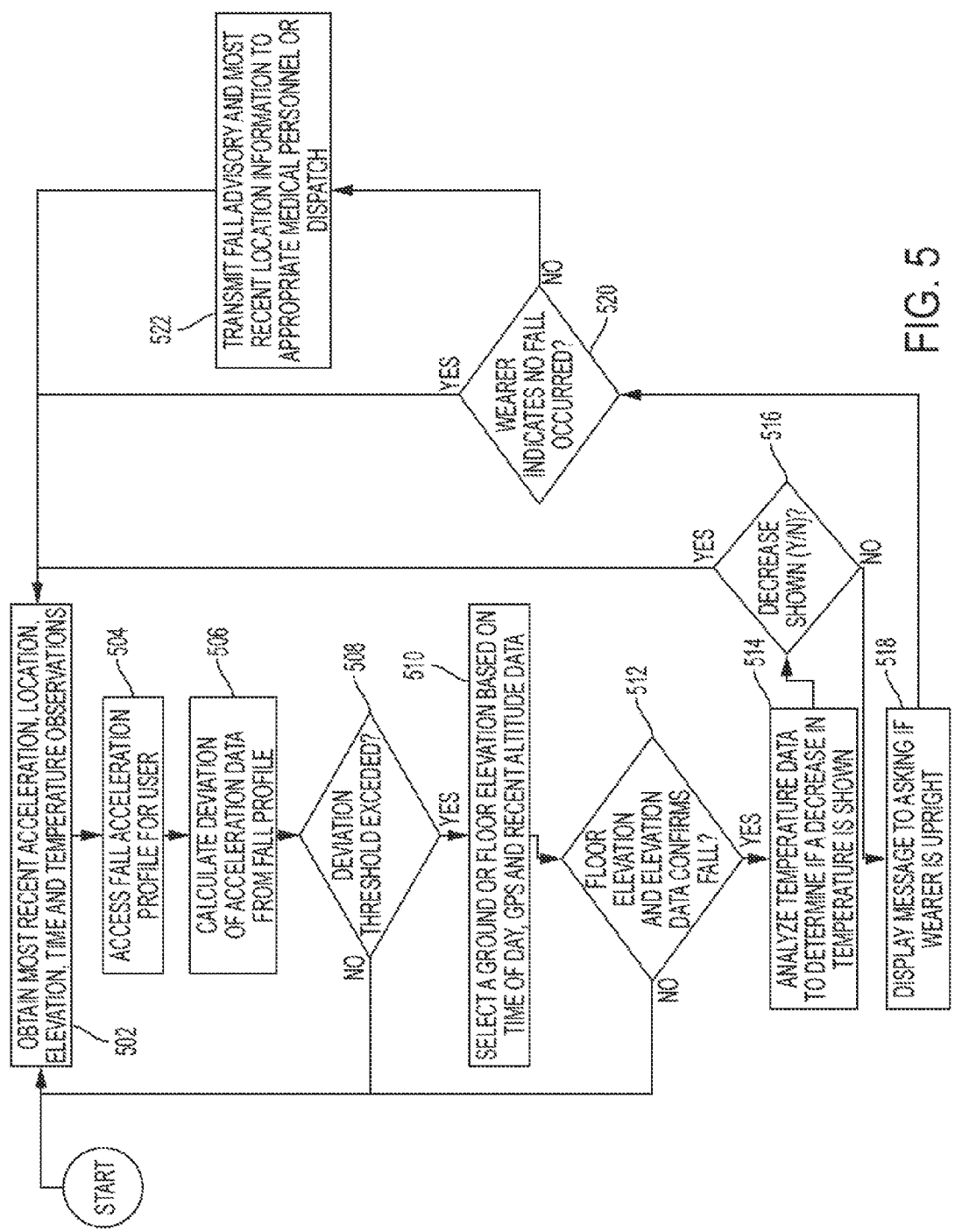
FIG. 5 is a flow chart illustrating an example sequence of fall detection operations that may be employed by the monitoring device disclosed herein.

FIG. 5 depicts an embodiment of generalized fall detection operations of the wrist-worn device 108. Specifically, FIG. 5 depicts one methodology by which the fall detection module 140 uses acceleration, elevation, and temperature data in the analysis performed in order to monitor the wearer's condition and detect falls. Additionally, FIG. 5 also depicts how the fall detection module 140 incorporates an activated fall profile and previously determined ground or floor elevation estimates in the monitoring process.

The depicted monitoring operations are begun at 502 by the fall detection module 140 obtaining most recent acceleration, location, altitude, time and temperature observations. At 504, the fall detection module 140 accesses the active fall acceleration profile stored within the wearer's profile. At 506, the fall detection module 140 calculates the deviation of the acceleration data from the fall profile.

At 508, the fall detection module 140 determines if the deviation calculated at 506 exceeds a similarity threshold. If the threshold is not exceeded, then the fall detection module 140 determines that the acceleration data is not indicative of a fall. In this case, the next step performed by the fall detection module 140 does not occur until subsequent acceleration data is registered. At this point, the fall detection module 140 obtains the most recent acceleration data, along with location altitude and time data, as depicted at 502, and the previously described steps are reiterated, as depicted.

However, if the fall detection module 140 determines that the deviation calculated at 506 does exceed the similarity threshold, then the acceleration data represents a possible fall, and the fall detection module 140 performs subsequent steps to confirm the possibility of a fall. For example, the fall detection module 140 selects an appropriate ground or floor altitude from the floor and surfaces data set 170, as depicted at 510. The fall detection module 140 selects an elevation based on the time of day, GPS data and recently observed elevation data. The selected elevation is chosen from amongst the surface and floor elevations previously determined and stored by the location and floor learning module 120. The manner in which the location and floor learning module 120 determines and stores surface and floor elevations will be described with reference to other drawings.

Subsequently, at 512, the fall detection module 140 determines whether the most recently registered altitude confirms the possibility of a fall detected at 508. This determination involves determining whether the most recently registered altitude data indicates that the wearer's elevation differs from the estimated floor or ground elevation by less than a threshold distance. If the difference is greater than the threshold, then the fall possibility hypothesis is rejected and the process reverts to step 502.

Conversely, if the difference is less than the threshold, the possibility of a fall is confirmed. In this case, the fall detection module analyzes temperature data at 514 to determine if a significant decrease in temperature is shown. If a substantial temperature decrease is shown (for example, if temperature decreases from approximately 98 degrees to 72 degrees, i.e. from body temperature to room temperature), then the fall possibility hypothesis is rejected because the drop in temperature is consistent with the wrist-worn device 108 having been detached from the wearer's body, and the acceleration data and altitude data that triggered the fall hypothesis at 506-508 and 512 is likely to be a result of the removal. In this case, the process reverts to step 502 so that subsequent monitoring can be performed on newly registered data.

However, if no such decrease is shown, then the fall detection module 140 activates the communications/warnings module 123 for the purpose of displaying a message which, as depicted at 516, asks the user if a fall has occurred. At this point, the interface display screen 165 is activated to receive a yes/no response from the user. When a response is received at 518 and the response confirms that a fall occurred, the communications/warnings module 123 activates an alert to be transmitted to medical personnel or an emergency dispatch service. This message includes the most recently obtained GPS location data and elevation data registered at the wrist-worn device 108, so as to assist emergency in locating the wearer.

Conversely, at 518, if the received response indicates that a fall has not occurred, the process continues at 502. In this way, the process repeats itself as new acceleration data is registered.

Figure 6:
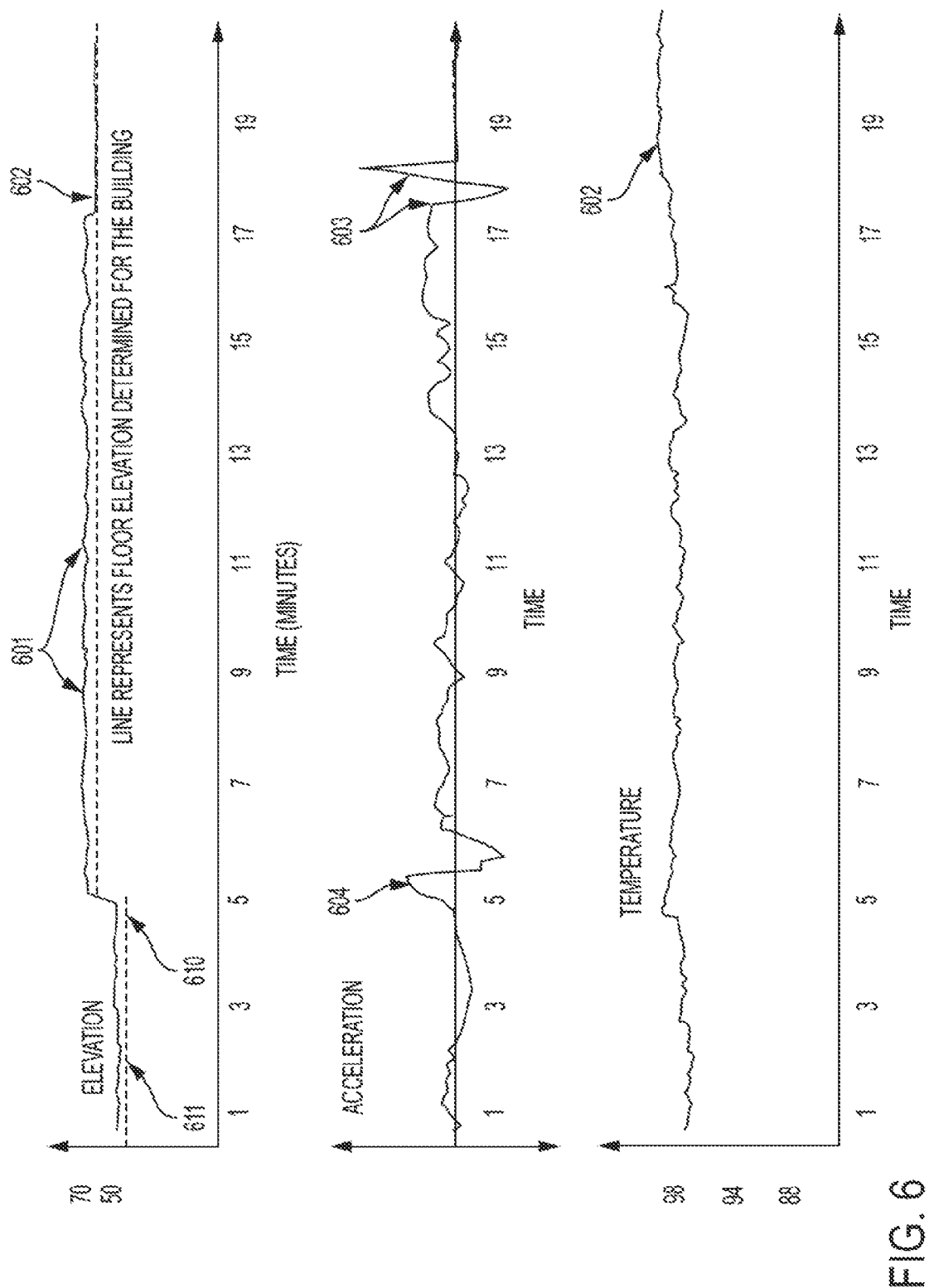
FIG. 6 display characteristics of acceleration, elevation and temperature data patterns that the monitoring device may recognize in order to detect falls.

FIG. 6 displays an example representation of techniques that the wrist-worn device 108 may use to analyze altitude, acceleration and temperature data, in combination, for fall detection purposes. The time series sensor data depicted in FIG. 6 is hypothetical only, and is presented only for purposes of showing, in a highly generalized and simplified manner, certain of the characteristics and patterns that may accompany a fall and be utilized by the fall detection module 140 to detect the fall.

The portion of elevation data at 611 is roughly unchanged, thereby suggesting that the wrist-worn device 108 is worn on a single floor of a building or on some flat ground between the first and fifth depicted minute. Because the average elevation is 50 feet during this time, the floor and surfaces learning module 120 estimates a floor elevation of approximately 47.5 feet, with the exact estimate depending on the wearer's height.

As depicted at 604, upwards acceleration has occurred, followed by downwards acceleration. Simultaneously, as depicted at 610, elevation data increases rapidly and then stabilizes within a tight range of values shown at 601. These patterns are consistent with the wrist-worn device 108 being worn on a higher floor of the building. In response to this increase in elevation and subsequent narrow range of observations centered around 70 feet, the floor and surfaces learning module 120 estimates a new floor elevation of 67.5 feet.

At 603, sharp downwards acceleration occurs, followed shortly thereafter by sharp upwards acceleration. The downwards and upwards acceleration closely matches the fall profile selected for the wearer. In this case, the fall detection module 140 hypothesizes that a fall has occurred, and attempts to confirm the hypothesis by analyzing elevation and temperature data.

At 602, the elevation data reveals a quick drop in elevation, followed by a narrow range of elevation observations. If the observations within the narrow range coincide closely with a floor elevation estimate for the building in which the monitoring device is worn (as suggested by the graph at 602), the fall detection module 140 may determine that the elevation data confirms the fall. Next, the fall detection module 140 analyzes the temperature data that coincides with acceleration data 603. The analyzed temperature data is shown at 602, and reveals no significant decline in temperature. The temperature is consistently equal to or slightly above normal body temperature, and therefore suggests that the wrist-worn device 108 is being worn. Thus the fall hypothesis based on acceleration data is confirmed by temperature and elevation data in the example case of FIG. 6. Accordingly, in such a situation, the communications/warnings module 123 may use the interface 165 to solicit fall confirmation from the wearer. Additionally, the communications/warnings module 123 may schedule the transmission of an emergency alert in case the fall is confirmed or a response is not received.

As mentioned previously, the wrist-worn device 108 may, at times, operate in an elevation learning mode which facilitates determining the elevation of floors and surfaces in the wearer's home, office, yard and other locations where the wearer spends significant amounts of time. The learned elevation information may be used by the fall detection module 140 to confirm the possibility of a fall when acceleration data closely matches with the active fall profile.

The elevation learning mode refers to a continuous process of data gathering, storage and analysis that the wrist-worn device 108 may execute upon sensing that is within a building, or upon determining that GPS location data and elevation data has been generally unchanged for a substantial period of time. It may be preferable that the wrist-worn device 108 be configured to operate in the elevation learning mode only during these two situations. In that way, the elevation data registered during activities such as walking outdoors and riding in a car does not affect the analysis used to determine the elevation of surfaces and floors in the buildings or areas in which the wearer spends significant amounts of time (e.g. house, office, backyard). Unchanging GPS location data and elevation data is commonly registered when the monitoring device is being worn in an environment such as a backyard or park in which a wearer could fall without other people being present.

During the elevation learning mode, elevation data is repeatedly registered, stored in a time series format, and analyzed. For example, elevation observations are be incrementally added to a data structure as they are obtained. At the same time that elevation data is registered and stored, GPS, temperature and time data is also registered and stored in respective data structures in a manner that parallels the elevation data structure. When the data structures have been filled or some other data sufficiency criteria is satisfied, the location and floor learning module 120 then analyzes the data together. If the data reveals an elevation of a floor, the elevation is added to the floor and surface elevation dataset 170 as a data point. In the floor and elevation data set 170, the elevation data point is represented as a floor elevation observation and is indexed to the building or geographic location in which the data underlying the observation was registered.

Figure 7B:
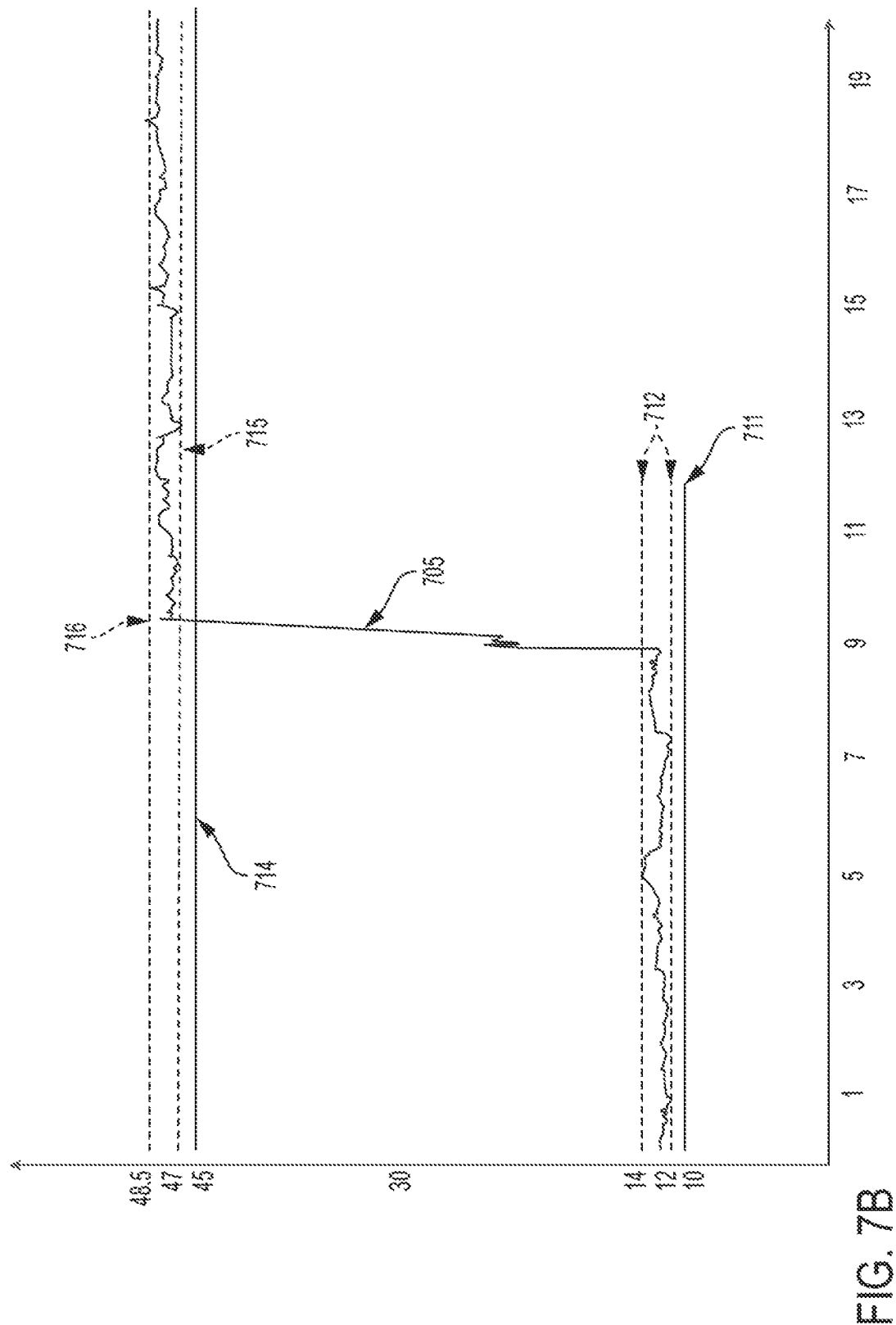

FIGS. 7A and 7B show visual representations of hypothetical elevation data to demonstrate how elevation data is gathered in the elevation learning mode and analyzed by the location and floor learning module 120 to learn the elevation of floors in a building. FIG. 7A is a time series display of elevation registered and stored over a course of 20 minutes, as indicated by the minute markings on the x-axis. Elevation observations are represented with respect to the y-axis, and various elevations (10, 12, 45, 47 and 48.5 feet are labeled on the y-axis). As may be understood by reference to data 704, the hypothetical elevation data indicates that the wrist-worn device 108 elevation varied within an approximately 2 foot range between the first elevation observation and the observation registered 9 minutes later. Subsequently, the elevation 705 of the monitoring device increased by approximately 35 within a 30 second period, starting at approximately the 9$^{th}$ minute of observations. After increasing rapidly, the elevation of the monitoring device stabilized at approximately 47 feet, and for the next 10 minutes the elevation 706 held steady within an approximately 1.5 foot range centered around 47 feet.

FIG. 7B is provided to show a generalized representation of the processing and analysis performed by the location and floor learning module. The analysis and processing is depicted with respect to the hypothetical elevation data of FIG. 7A, and is intended to show how learning steps and methods can be used to estimate floor elevations for the building in which elevation data is registered.

For example, FIG. 7A demonstrates how a location and floor learning module 120 scans the data so as to identify significant periods of time in which the majority of elevation observations fell within a single, narrow elevation range. Most individuals, when inside their home or building, rarely raise their wrists above their heads, and normally do so only momentarily. Similar, most people rarely move their wrists within approximately 1.5 feet of the ground, and when they do lower their wrists below that height, it is normally for a brief period of time. Thus, it is reliable to assume that the wearer's wrists will almost always be within approximately 2-5 feet of any home or office floor on which the wearer is present.

For this reason, the location and floor learning module 120 scans the data in search of a series of elevation observations in which the majority of observations fall within a 3 foot range. When such a range is found, the location and floor learning module 120 makes a floor elevation estimate based on the lower elevation of the range. For example, if a series of observations falls within 12-14 feet, as indicated at 712, a floor in the building is estimated to have an elevation of 10 feet.

Similarly, when the wrist-worn device 108 is being worn within a building, a rapid elevation change of at least 12 feet may be expected to coincide with walking up or down stairs or entering an elevator. Thus, for example, the location and floor learning module may deduce that the user has changed floors in response to detecting an increase in elevation, such as the increase depicted at 705. Moreover, such an elevation increase (or decrease) will normally be followed by a prolonged period of consistent elevation observations falling within another 2-5 foot range, as depicted by the lines at 715 and 716. The location and floor learning module 120 may be configured to scan for these additional 2-5 foot ranges, and to recognize such ranges as representative of user activity on a different floor of the building. The location and floor learning module makes additional floor elevation estimates when such ranges are found, so that floor elevation information may be used in monitoring the wearer's condition on various floors. For this reason, a line 714 at 45 feet is provided to demonstrate how the location and floor learning module 120 might use the range of observations falling between 47 and 48.5 feet. Thus, it should be understood that the location and floor learning module may be configured to learn multiple different floor elevations within any one building.

In addition to analyzing elevation data in the manner described with respect to FIG. 7B, the location and floor learning module 120 may additionally or alternatively perform multi-variable analysis to learn the elevations of floors and surfaces. For example, temperature data is analyzed in conjunction with contemporaneous elevation data to learn the elevations of table or countertop surfaces within a building. When a table or countertop surface elevation is learned, the elevation is used to confirm estimated elevations of floors in the building.

Figure 8:
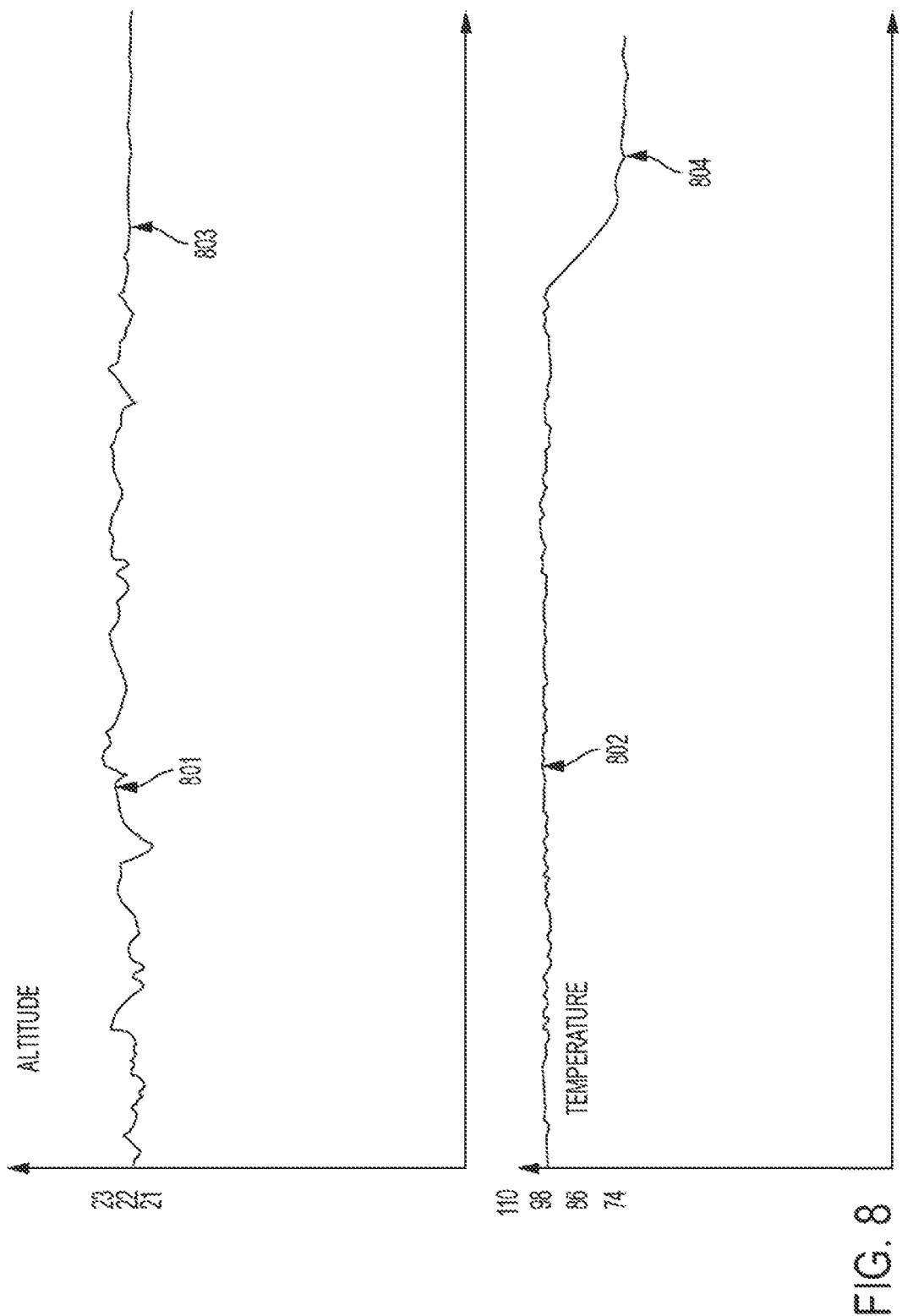
FIG. 8 presents examples of patterns in elevation data and temperature data which the monitoring device may recognize in order to determine elevations of surfaces and floors beneath a wearer.

FIG. 8 depicts example elevation and temperature data patterns that the location and floor learning module scans for and uses to learn surface elevations. FIG. 8 shows 30 minutes of elevation data and contemporaneously registered temperature data. A first data pattern is the continuous and narrow (approximately 2-3 foot) range of elevation observations depicted at 801. As described previously with regards to FIG. 7A, patterns such as range 801 may be interpreted as resulting from the monitoring device being worn by a wearer who is involved in normal activity on a single building floor. The series of elevation data corresponding to range 801 is contemporaneous with a series of temperature observations 802 that fall within a narrow range centered around 98 degrees—the normal human body temperature. Thus, the location and floor learning module 120 may interpret temperature range to confirm that the wrist-worn device 108 is being worn, and that the wearer is involved in normal activity on a single floor of the building.

An additional data pattern begins at 803. This pattern is marked by the elevation observations becoming more consistent than in data pattern 801. Additionally, the pattern beginning at 803 is marked by the average elevation observation being approximately equal to the average elevation observation in data pattern 801. Data pattern 803 may be interpreted as being caused by the wrist-worn device 108 being removed from the wearer's body and being placed on a night stand, table or other surface having an elevation between 2-4 feet above the floor elevation.

An additional temperature data pattern 804 can be interpreted as confirming the interpretation of pattern 803. Temperature pattern 804 is characterized by a rapid fall in temperature, from 98 degrees (body temperature) to approximately 72 degrees (room temperature), followed by a series of temperature observations within a narrow observational range centered about approximately 72 degrees. Moreover, the time at which the fall in temperature was registered coincided with the beginning of pattern 803, at which time the elevation observations became more consistent.

Figure 9:
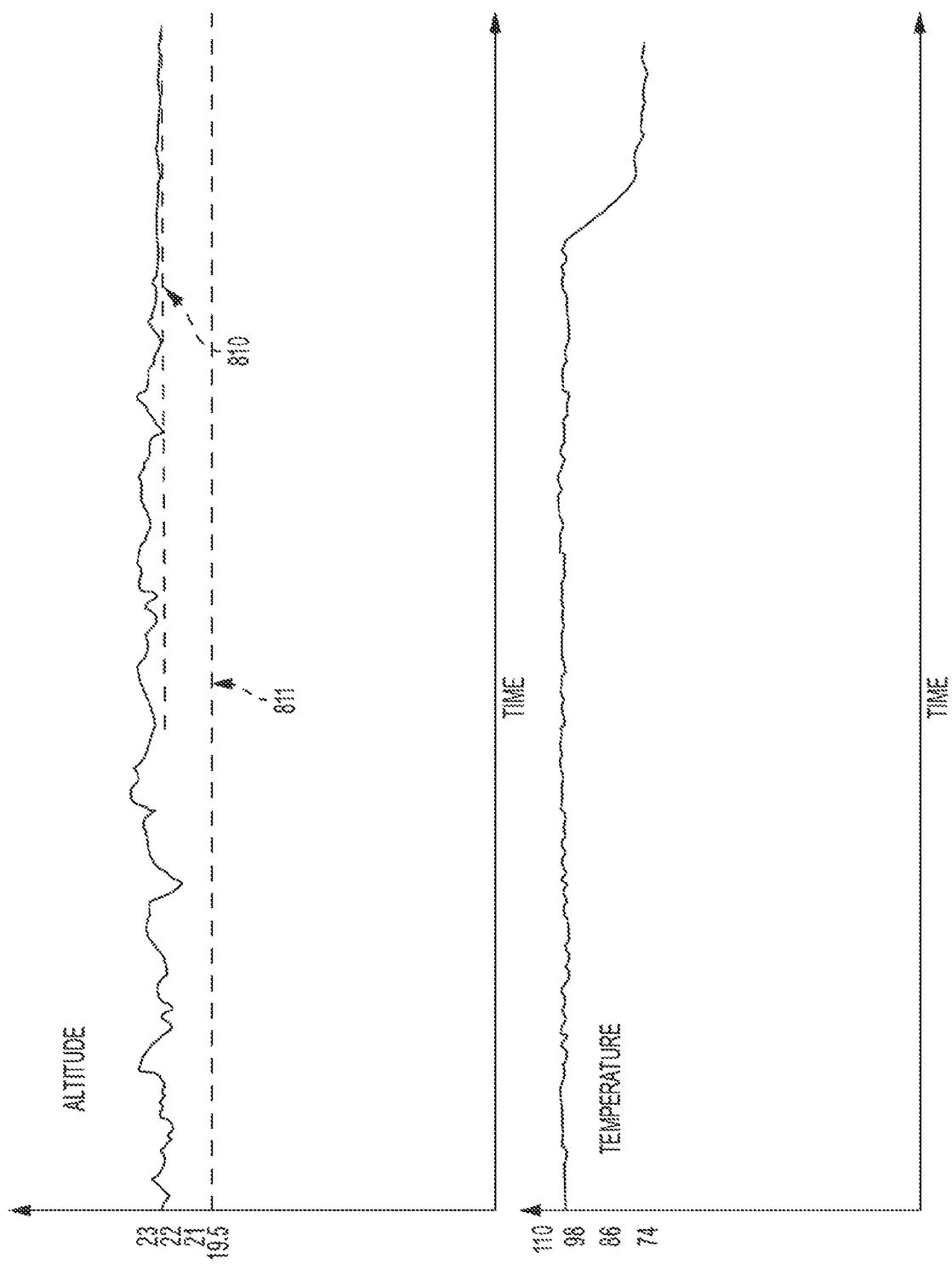
FIG. 9 illustrates how the monitoring device may determine surface and floor elevations based on patterns in temperature and elevation data.

The location and floor learning module 120 may make both floor and surface elevation estimates based on a series of data patterns such as 801, 802, 803, and 804. One manner of making such estimates is depicted in FIG. 9. Because removal of the monitoring device and placement on a nightstand or table is suggested by data pattern 803 following closely after pattern 801, and confirmed by temperature data pattern 804 following immediately after pattern 802, the location and floor learning module 120 may estimate a surface elevation directly from the elevations indicated by pattern 803. This estimation is represented by line 810, which directly coincides with the observations of data pattern 803. Line 810 is intended to show an estimated surface elevation of 21.5 feet.

Additionally, the location and floor learning module 120 may estimate a floor elevation based on the surface elevation 810 and the lower elevation of the range of observations associated with elevation data pattern 801. For example, based on an assumption that most nightstand tables stand 2 feet off the ground and an assumption that most people rarely move their wrists within 1.5 feet of the ground, data patterns 801 and 803 may be jointly interpreted as revealing that a floor at an elevation of 19.5 is immediately below the wrist-worn device 108. This floor elevation estimation is represented by the line at 811.

FIGS. 8 and 9, as described above, provide certain example data patterns that may be detected with respect to temperature data and used to determine floor and surface elevations. However, the scope of this disclosure is further intended to cover the detection and use of other data patterns and data pattern combinations which contain information about surface and floor elevations. These additional data patterns, although not specifically described herein, may be patterns involving other data besides elevation and temperature data. For example, GPS and time data may be used in conjunction with elevation data to make surface and floor estimates, and any such detectable and informative patterns as may be provided by such data shall be understood to be within the scope of this disclosure.

Figure 10:
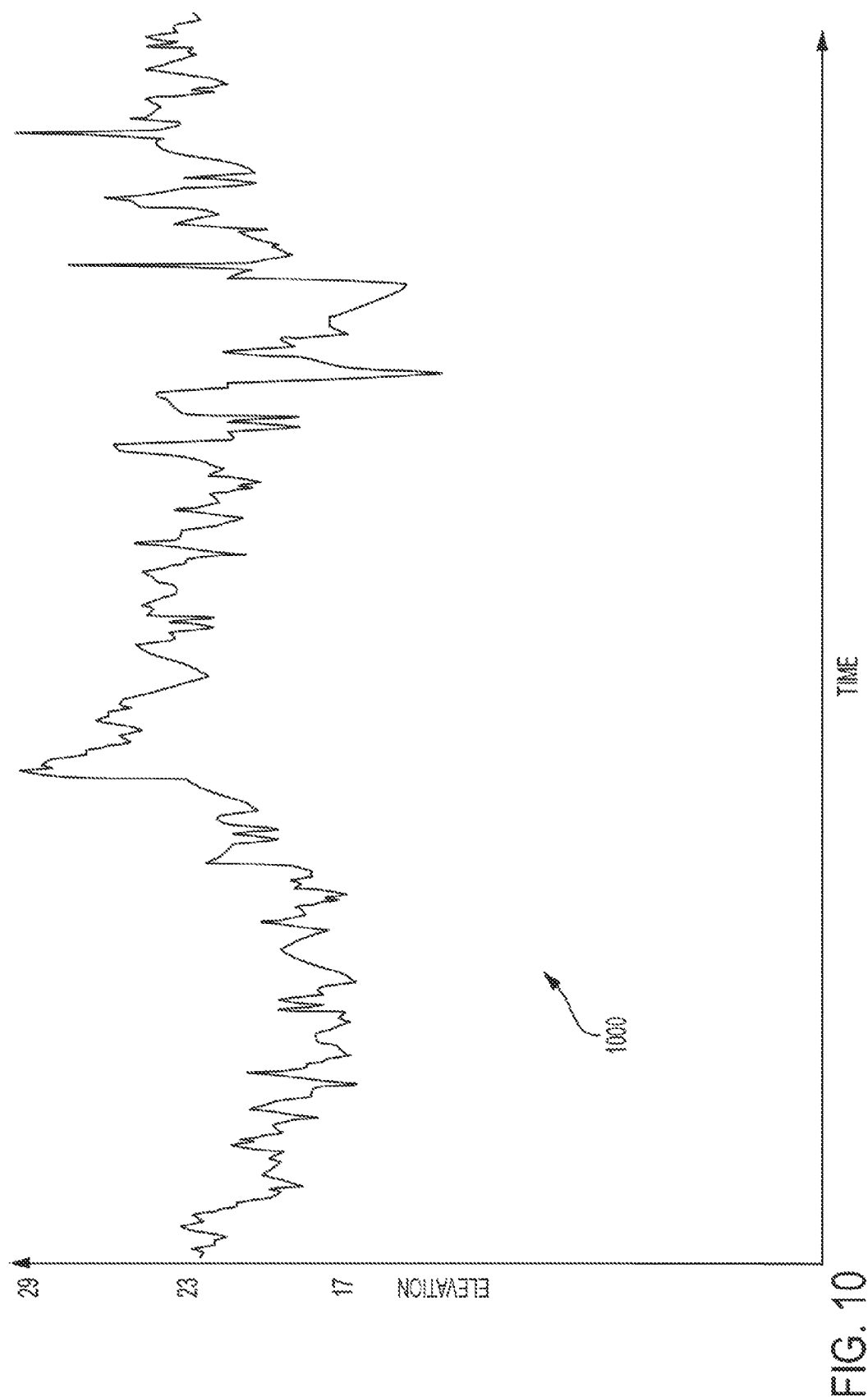
FIG. 10 illustrates characteristics of noisy elevation data that the monitoring device may recognize in order to determine that elevation data is temporarily unreliable for determining surface and floor elevations.

The location and floor learning module 120 may further include features enabling it to recognize noisy elevation data during the elevation learning mode, and determine that floor and surface elevation estimates should not be made because of the risk of unreliability. A noisy elevation data pattern of this sort is depicted at 1000 in FIG. 10. The time series elevation data pattern 1000 is distinguishable by the fact that it contains no continuous ranges of elevation observations falling within a 2-4 foot range. Moreover, the elevation changes are frequent and large. An elevation data pattern of this sort may be caused by changing environmental or building ventilation conditions, or by the user engaging in activity such as exercise or calisthenics. It may also be an indication that the wrist-worn device 108 is on a roadway or is no longer within a building.

The location and floor learning module 120 stores each floor and surface estimate in the floor and surfaces elevation data set 170. In this way, floor and surface estimates made in a same building may be used together to generate refined determinations of the floor and surface elevations, and the refined determinations are ultimately used in the fall detection process.

The location and floor learning module 120 may use clustering and averaging, or some other similar technique to generate the refined determinations. The clustering enables grouping of elevation estimates made with respect to a same surface or floor. For example, if the wrist-worn device 108 is used to monitor a wearer who lives on the third floor of an apartment having an elevation of 80 feet, the location and floor learning module 120 may make several elevation estimates of approximately 80 feet.

Hypothetically, the wearer might make frequent visits to a friend's apartment in the same building, 50 feet above the wearer's. In this case, the location and floor learning module 120 may make several elevation estimates of approximately 130 feet. The estimates that correspond to the friend's apartment should not be allowed to affect the refined determination of the floor elevation in the wearer's apartment, and vice versa. By clustering elevation estimates prior to generating a refined elevation determination, the location and floor learning module 120 ensures that elevation estimates made with respect to one floor or surface are not affected by estimates made with respect to another floor or surface.

Clustering analysis may involve grouping floor elevation observations using a clustering algorithm such as k-means, and separately grouping surface elevations using the same algorithm. When a cluster has a significant number of observations and is significantly focused (e.g. has a dense concentration of data), the average elevation estimate in the cluster is stored as a refined determination of either a floor or surface elevation.

Figure 11:
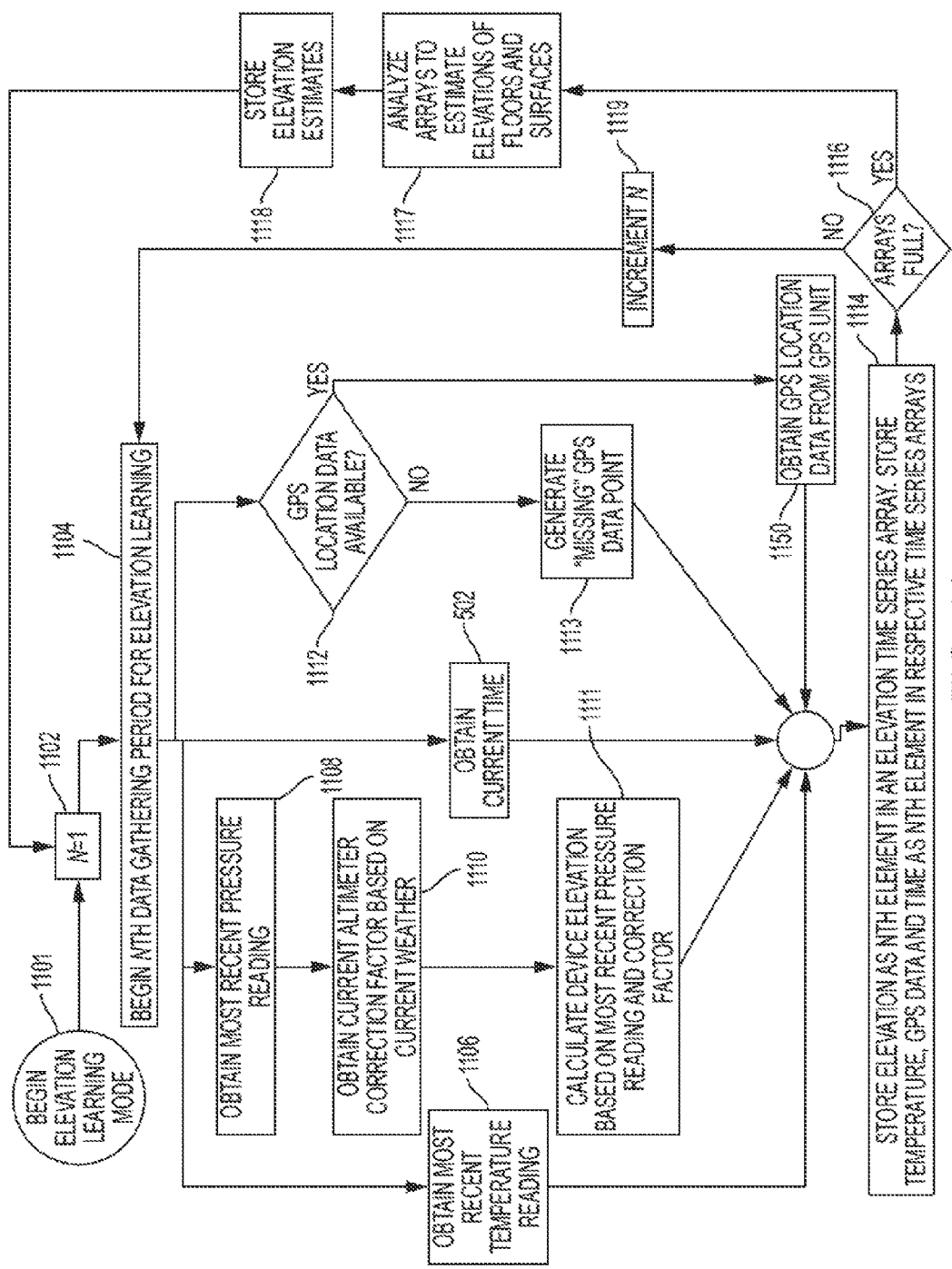
FIG. 11 is a flow chart illustrating an example sequence of operations that may be employed by the monitoring device while operating in the elevation learning mode.

FIG. 11 is a flow chart depicting an example sequence of operations that the wrist-worn device 108 uses to perform data gathering, storage, and analysis in the elevation learning mode. At 1101 the wrist-worn device 108 has already entered the elevation learning mode, and begins the data gathering and analysis process. A variable N is initialized to 1 at 1102. The variable N is a count variable that the wrist-worn device 108 uses to track how much data has been gathered so as to determine when data analysis may be performed. At 1104, the Nth data gathering period begins. The data gathering involves four parallel processes.

One of the processes involves accessing the most recent temperature reading provided by the thermometer, as depicted at 1106. A second parallel process involves obtaining the most recent pressure reading provided by the altimeter and the current altimeter correction factor based on the current weather, as shown at 1108 and 1110. The second parallel process further involves calculating the wrist-worn device 108 elevation based on the recent pressure reading and the correction factor, as shown at 1111.

The third parallel process is performed to obtain GPS data that is contemporaneous with the elevation data and temperature data registered in the second and third parallel process explained previously. However, GPS data is frequently unavailable in the indoor environment. Thus, at 1113, the wrist-worn device 108 generates a "missing" GPS data point if GPS data is determined to be unavailable at 1112. However, if the GPS location data is available, it is obtained for storage, as depicted at 1150. The fourth parallel process involves determining the current time for the purpose of time stamping the GPS, elevation and temperature data.

At 1114, the elevation data is stored as the Nth element in an elevation time series array, or other similar time series data structure. Also, at 1114, the wrist-worn device 108 stores the most recent temperature, GPS data and time data in respective time series arrays.

At 1116, if the arrays are not yet full, then the parallel data gathering and storage steps are repeated again, starting at step 1106. The process repeats until the arrays are filled. When the wrist-worn device 108 determines that the arrays are full at 1116, then the location and floor learning module 120 analyzes the arrays for any data patterns that suggest the elevation of a floor or surface. The location and floor learning module 120 makes elevations estimates if suitable data patterns exists, as depicted at 1117. If elevation estimates are made, they are stored in the floor and surfaces elevation data set, as depicted at 1118, and are used in combination with previous estimates made in the same building for the purpose of generating refined elevation determinations (not shown in FIG. 11). Subsequently, the entire data gathering, storage and analysis process may be repeated.

Figure 12:
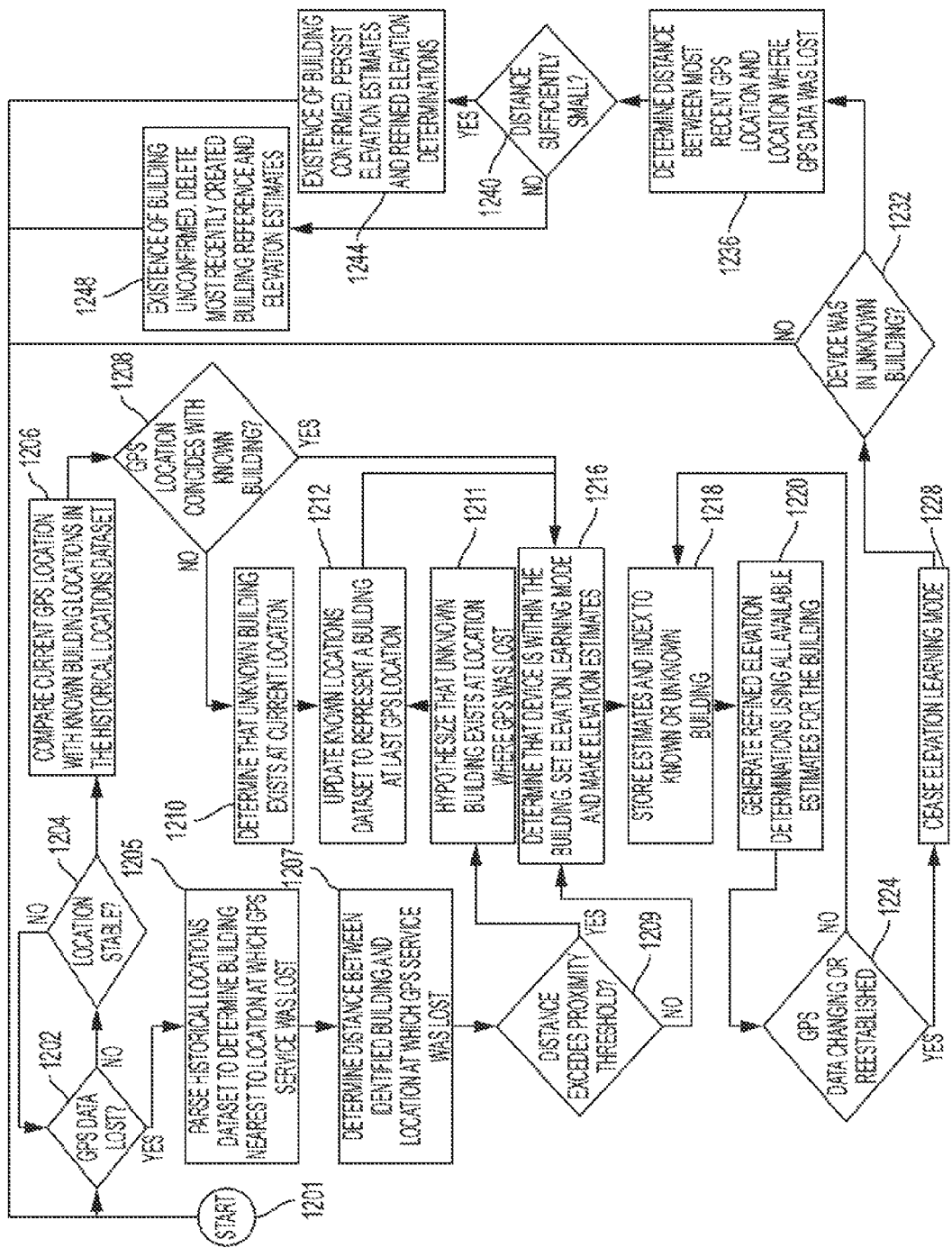
FIG. 12 is a flow chart illustrating an example sequence of building detection and elevation learning operations that may be employed by the monitoring device.

FIG. 12 is a flow chart that provides a simplified depiction of example operations that the wrist-worn device 108 may use to learn the locations of buildings, detect when it has been brought into a building, and activate and deactivate the elevation learning mode as appropriate.

The example operations depicted in FIG. begin at 1201. At 1202 and 1204, if GPS data is not lost and the GPS data indicates the wrist-worn device 108 position is generally unchanging, the location and floor learning module 120 compares the current GPS location with the locations of known buildings in the historical locations data set 180. This comparison is depicted at 1206. At 1208, if the GPS location does not coincide with a known building, the location and floor learning module 120 hypothesizes, as depicted at 1210, that an unknown building exists at the current monitoring device location. Subsequently, at 1212, the location and floor learning module 120 updates the historical locations dataset 180 so as to include a reference to the hypothesized building.

A different operational sequence may alternatively lead to step 1212. As depicted at 1205, if GPS data is lost at 1202, the location and floor learning module 120 parses the historical locations dataset 180 to determine the known building located closest to where GPS data was lost. At 1207, the locations and floors learning module 120 determines the distance between this known building and the location at which GPS data was lost. At 1209, the distance is compared to a proximity threshold. If the distance exceeds the threshold, then locations and floors learning module 120 hypothesizes that an unknown building exists at the location where GPS data was lost. Step 1212 is then executed in response.

Conversely, if the distance is less than the threshold at 1209, the location and floor learning module 120 determines that the wrist-worn device 108 is within the known building that was referenced as part of the comparison at 1207. Accordingly, the elevation learning mode is activated, and elevation estimates are made at 1216. At 1218, the location and floor learning module 120 stores elevation estimates in the floor and surfaces data set 170. The observations are indexed to the known or unknown building, whichever the case may be. At 1220, the refined elevation determinations are made using all available elevation estimates indexed to the building. The elevation learning mode then continues, with steps 1218-1220 being continuously repeated in sequence. Ad depicted at 1224 the repetition of steps 1218-1220 continues until either the GPS indication becomes unstable (for example, the wearer gets in a car and leaves the building) or GPS date again becomes available if it had previously been unavailable.

At 1228, the elevation learning mode is ceased because either resumption of GPS service or rapidly changing GPS data indicates that the wearer may have left the building. At 1232, if the wrist-worn device 108 had sensed that it was in a building that had been recognized from the historical locations data set 170, the process reverts to 1202, and GPS data is further analyzed to detect building reentry, or entry into a different building.

However, if the location and floor learning module 120 had hypothesized (at 1210 or 1211) an unknown building, then a series of additional checks are made which help confirm that presence within a building was accurately sensed. For example, at 1236 the location and floor learning module 120 compares the distance between the most recent GPS location and the location where GPS data was lost. At 1240, if this distance is sufficiently small, then the hypothesized building is confirmed. Accordingly, the elevation estimates and refined elevation determinations made at 1216-1220 are persisted in memory. If, at 1240, the distance is not sufficiently small, then the existence of the hypothesized building is unconfirmed. For this reason, the elevation estimates and refined elevation determinations are deleted. Regardless of the outcome at 1240, the entire process of FIG. 12 is continuously reiterated, as depicted by the arrows returning to step 1202.

Figure 13:
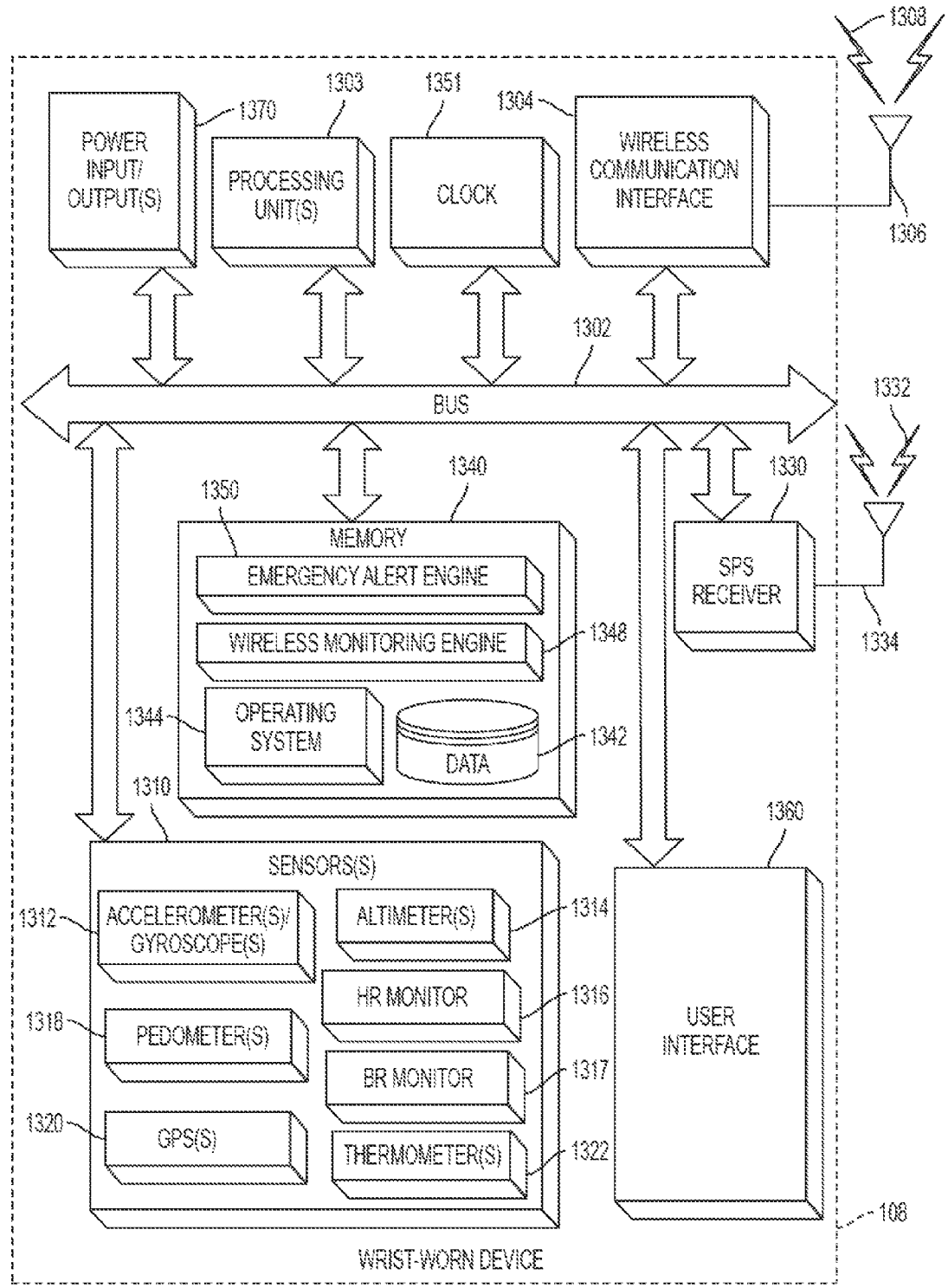
FIG. 13 depicts an example wrist-worn device, in accordance with at least one embodiment.

FIG. 13 depicts an example of the wrist-worn device 108. It should be noted that FIG. 13 is meant only to provide a generalized illustration of various components, any or all of which may be utilized as appropriate. In some embodiments, some or all of the components included in the wrist-worn device 108 can be include don the wristband monitoring device 110 or may also or instead be located on the faceplate device 112. In some embodiments, some or all of the components shown in FIG. 1B can also be included in the wrist-worn device 108 of FIG. 14. Moreover, system elements may be implemented in a relatively separated or relatively more integrated manner.

The wrist-worn device 108 is shown comprising hardware elements that can be electrically coupled via a bus 1302 (or may otherwise be in communication, as appropriate). The hardware elements may include a processing unit(s) 1303 which can include without limitation one or more general-purpose processors, one or more special-purpose processors (such as digital signal processors (DSPs), application specific integrated circuits (ASICs), and/or the like), and/or other processing structure or means, which can be configured to perform one or more of the methods described herein.

The wrist-worn device 108 might also include a wireless communication interface 1304, which can include without limitation a modem, a network card, an infrared communication device, a wireless communication device, and/or a chipset (such as a Bluetooth device, an IEEE 802.11 device, an IEEE 802.15.4 device, a WiFi device, a WiMax device, cellular communication facilities, etc.), and/or the like. The wireless communication interface 1304 may permit data to be exchanged with a network, wireless access points, other computer systems, and/or any other electronic devices described herein. The communication can be carried out via one or more wireless communication antenna(s) 1306 that send and/or receive wireless signals 1308. For example, the wireless signals 1308 can be cellular network signals or a Bluetooth connection. In at least one embodiment, wristband monitoring device 110 may communicate with the wrist-worn device 108 via the wireless communication interface 1304.

Depending on desired functionality, the wireless communication interface 1304 can include separate transceivers to communicate with base transceiver stations (e.g., base transceiver stations of a cellular network) and access points. These different data networks can include, an Othogonal Frequency-Division Multiple Access (OFDMA), Code Divisional Multiple Access (CDMA), Global System for Mobile Communications (GSM), and/or other types of networks.

The wrist-worn device 108 can further include sensor(s) 1310. Such sensors can include, without limitation, one or more accelerometer(s) and/or gyroscope(s) 1312, altimeter(s) 1314, heart rate monitor(s) 1316, pedometer(s) 1318, GPS(s) 1320, thermometer(s) 1322, blood pressure monitor(s) 1317, and the like (e.g., glucose monitor, oxygen saturation monitor). At least a subset of the sensor(s) 1310 can provide readings used to provide wellness monitoring as described herein.

Embodiments of wrist-worn device 108 may also include a Satellite Positioning System (SPS) receiver 1330 capable of receiving signals 1332 from one or more SPS satellites using an SPS antenna 1334. The SPS receiver can receive satellite data that can be transmitted to the GPS sensor 1320. The satellite data can be information sufficient to allow the GPS sensor 1320 to determine a geographic location of the wristband monitoring device based on the satellite data. Such positioning can be utilized to complement and/or incorporate the techniques described herein. It can be noted that, as used herein, an SPS may include any combination of one or more global and/or regional navigation satellite systems and/or augmentation systems, and SPS signals may include SPS, SPS-like, and/or other signals associated with such one or more SPS.

The wrist-worn device 108 may further include or be in communication with a memory 1340. The memory 1340 is an example of a computer-readable storage media. In at least one example, computer-readable storage media include volatile or non-volatile, removable or non-removable media implemented in any method or technology for storage of information such as computer-readable instructions, data structures, program modules, or other data. Additional types of computer storage media that may be included in the wrist-worn device 108 may include, but are not limited to, PRAM, SRAM, DRAM, RAM, ROM, EEPROM, flash memory or other memory technology, CD-ROM, DVD or other optical storage, magnetic cassettes, magnetic tape, magnetic disk storage or other magnetic storage devices, or any other medium which can be used to store the desired information and which can be accessed by the wrist-worn device 108. Combinations of any of the above should also be included within the scope of computer-readable memory 1340 can further be used to store sensor data for any combination of sensors 1310 in data store 1342.

As used herein, medical-related data can include, for example, health information that is created or received by a health care provider, a processed or unprocessed version of medical data detected by medical equipment, and/or user-identified data. Medical-related data can include information that identifies a patient, such as personal information and/or demographic information. For example, the information can identify a patient's name, age, sex, race, physical address, phone number, email address and/or social security number. Medical-related data may include information collected by a health plan, a public health authority, an employer, a life insurer, a school or university, or a health care clearinghouse that relates to the past, present, or future physical or mental health or condition of any individual.

Medical-related data can include financial and/or insurance information corresponding to the patient. For example, the information can identify an insurance company, insurance plan, member identification number, group number, insurance contact information (e.g., address and/or phone number), deductible information, out-of-pocket information, copay information, an employer, an occupation and/or salary information.

Medical-related data can include medical-history information, such as past diagnoses, past or present symptoms or past procedures and/or corresponding dates (e.g., of diagnoses, symptom initiations and/or procedures). Medical-related data can identify past or present medications being taken by or having been prescribed to the patient and corresponding dates. In some examples, the medical-related data can identify orders pharmacology orders, whether associated with a patient, doctor, or otherwise.

Medical-related data can include an identification of one or more medical services being or having been requested by a patient. A medical service can include, for example, an evaluation performed by a medical care professional, a medical test, a surgery and/or other procedure. Medical-related data can identify a medical test or analysis that was performed or prescribed and/or a result of the test or analysis. For example, information can indicate that a test (e.g., lab test, MRI, x-ray, CT scan, echocardiography, EKG, EEG, EMG, or ultrasound) was performed on a particular date and/or by a particular entity and can further include a processed and/or unprocessed result of the test (e.g., a count or level; an indication as to whether a test result is normal; and/or an indication as to whether a particular feature (e.g., a fracture, tumor, lesion, slowed nerve conduction) was observed and/or a magnitude of the feature).

Medical-related data can identify one or more care providers or institutions. The care provider and/or institution can be one associated with recent or past care and/or with the patient. For example, data can be transmitted for a patient admitted in Hospital A and being treated by Specialist B, though the data can also identify that the patient's primary care physician is Doctor C.

Medical-related data can identify one or more emergency contacts or family members and contact data for the individuals. For example, medical-related data can identify that the patient's emergency contact is an adult child that may be contacted at a provided phone number.

Medical-related data can identify a patient healthcare directive. For example, medical-related data can identify if the patient has a living will, a do not resuscitate order (DNR), or if another individual has the right to make medical decisions relating to the patient's medical care.

Medical-related data may further include one or more authorized viewers. Authorized viewers are those that the user has agreed to allow access to his medical-related data. For example, a user may authorize a doctor, an individual having rights to make medical decision related to the patient's medical care, a medical institution, and the like to access his medical-related data. The user may indicate that the authorization is contingent on certain events transpiring (e.g., an emergency situation).

Medical-related data may, or may not, selectively pertain to a particular patient. For example, non-patient-specific data may include a price of a prescription, a recommended or approved dosing schedule for a medication, a work schedule for a physician, an acceptance criteria for a clinical study, Non-patient-specific data can include information pertaining to the operation of a medical care facility, financial information, administrative information, and generic clinical information.

Medical-related data can, depending on the implementation, include individually identifiable health information and/or de-identified information. Individually identifiable health information includes, for example, health information, including demographic information collected from an individual that is created or received by a health care provider, health plan, employer, or health care clearinghouse; and that relates to the past, present, or future physical or mental health or condition of an individual, the provision of health care to an individual, or the past, present, or future payment for the provision of health care to an individual; and that identifies the individual; or, with respect to which there is a reasonable basis to believe, can be used to identify the individual. De-identified information includes information that cannot be used on its own or with other information to identify a person to whom the information belongs. De-identified information can include normal ranges or values associated with various sensor data based on gender, age, or other classification. De-identified information can also include medical-related data aggregated from other wrist-worn device users or non-users related.

As used herein, medical-related data can include protected health information, which can include individually identifiable health information that is transmitted by electronic media, maintained in electronic media, or transmitted or maintained in any other form or medium. Examples of protected health information, include, for example any information about health status, provision of health care, or payment that can be linked to a particular patient and may include any of the following information capable of identifying the patient: names, geographic identifiers, dates directly relating to the patient, phone numbers, fax numbers, email addresses, social security numbers, medical record numbers, health insurance beneficiary numbers, account numbers, certificate/license numbers, vehicle identifiers and serial numbers, device identifiers and serial numbers, web Uniform Resource Locators, Internet Protocol addresses, biometric identifiers (e.g., finger, retinal, and voice prints), full face photographic images and any comparable images, and any other unique identifying number, characteristic, or code.

Turning to the contents of the memory 1340 in more detail, the memory 1340, in at least one embodiment, includes an operating system 1344 and one or more application programs, modules, or services for implementing the features disclosed herein. For example, the contents of the memory 1340 can include a wellness monitoring engine 1348 and an emergency alert engine 1350. In some aspects, a fall detection module or fall detection engine can also be located in the memory 1340. In at least one example embodiment, the wrist-worn device 108 is configured to receive, store, and/or display content and at least one interface for interacting with the service provider computers 116 and users. Additionally, the memory 1340 stores access credentials and/or other user information such as, but not limited to, user IDs, passwords, and/or other user information. In some examples, the user information includes information for authenticating an account access request such as, but not limited to, a device ID, a cookie, an IP address, a location, or the like. Additionally, the user information includes information regarding a therapy associated with the user.

The memory 1340 of the wrist-worn device 108 also can comprise software elements (not shown), device drivers, executable libraries, and/or other code, such as one or more application programs, which may comprise computer programs provided by various embodiments, and/or may be designed to implement methods, and/or configure systems, provided by other embodiments, as described herein. Merely by way of example, one or more processes described with respect to the method(s) discussed above might be implemented as code and/or instructions executable by the wrist-worn device 108 (and/or processing unit(s) 1303 within a wrist-worn device 108) and/or stored on a non-transitory and/or machine-readable storage medium (e.g., a "computer-readable storage medium," a "machine-readable storage medium," etc.). In an aspect, then, such code and/or instructions can be used to configure and/or adapt a general purpose processor (or other device) to perform one or more operations in accordance with the described methods.

Wrist-worn device 108 112 may include clock 1350. Clock 1350 is used to generate a time stamp for each of the data observations generated by the sensors. The time stamps are used by the processing units 1303 in the analysis of sensor data, and facilitate pattern recognition and improved capacity for determining the operational environment of the wrist-worn device 108. The clock 1350 can also be used by the processing units 1303 to for alarms and other standard clock functions.

The wrist-worn device 108 includes a user interface 1360. User interface 1360 may include a touchscreen, a button, a keypad interface, a vibration generator, a sound generator, and/or other similar interface. The interface facilitates soliciting information from the wearer and obtaining input data and information provided by the wearer in response. The interface can also facilitate receiving an indication from the wearer that an emergency situation is affecting the wearer. For example, the user interface 1360 can be a button that when pressed indicates the wearer is experiencing an emergency situation. In some aspects the user interface 1360 can be a touchscreen that can be an emergency indicator that determines the user is experiencing an emergency in response to the wearer pressing the touchscreen for a pre-determined period of time. The touchscreen can change colors to indicate that the wearer is experiencing an emergency (for example, the touchscreen can turn red). Additional user interfaces can be included in the wrist-worn device 108, for example the wrist-worn device 108 can include a touchscreen used to solicit information from the wearer and a button both that is an emergency indicator.

The wrist-worn device 108, utilizing user interface 1360, solicits information about the user or the user's condition or environment so as to analyze such data in order to provide the wellness monitoring features discussed herein. For example, wrist-worn device 108 utilizes user inputs via user interface 1360 to obtain information about the user's physique, lifestyle, health, activity level as well as information related to therapy compliance and other information relevant to ascertaining the user's overall wellness. The wrist-worn device 108 further solicits any inputs that may facilitate improved learning, analysis and sensing performed by the wrist-worn device 108, and/or other suitable devices or computers (e.g., service provider computers 116).

The wrist-worn device 108 includes an energy source indicated by power input/outputs 1370. In some aspects, the faceplate device 112 of the wrist-worn device 108 includes an energy source a means to charge said energy source, and a means to charge an energy source located on wristband monitoring device 110. The energy source may be a battery, a capacitor, or any other suitable means for storing chemical or electrical energy for later use. In at least one embodiment, wristband monitoring device 110 may be connected to faceplate device 112 and the battery of the faceplate device 112 may charge the battery of wristband monitoring device 110. In some embodiments, wristband monitoring device 110 may be connected to the faceplate device 112 and the battery of faceplate device 112 may be the energy source for the wristband monitoring device 110 or vice versa. The wrist-worn device 108 may be configured to charge from a standard A/C adaptor, or by use of a charging dock (e.g., a charging cradle) configured to house the faceplate device 112, or other suitable charging means. The wrist-worn device 108 can also monitor the power level of the wrist-worn device 108 (e.g., the battery level when a battery is the power source). The user interface 1360 can facilitate alerting the wearer that the power level of the wrist-worn device 108 is below a pre-set threshold.

Figure 14:
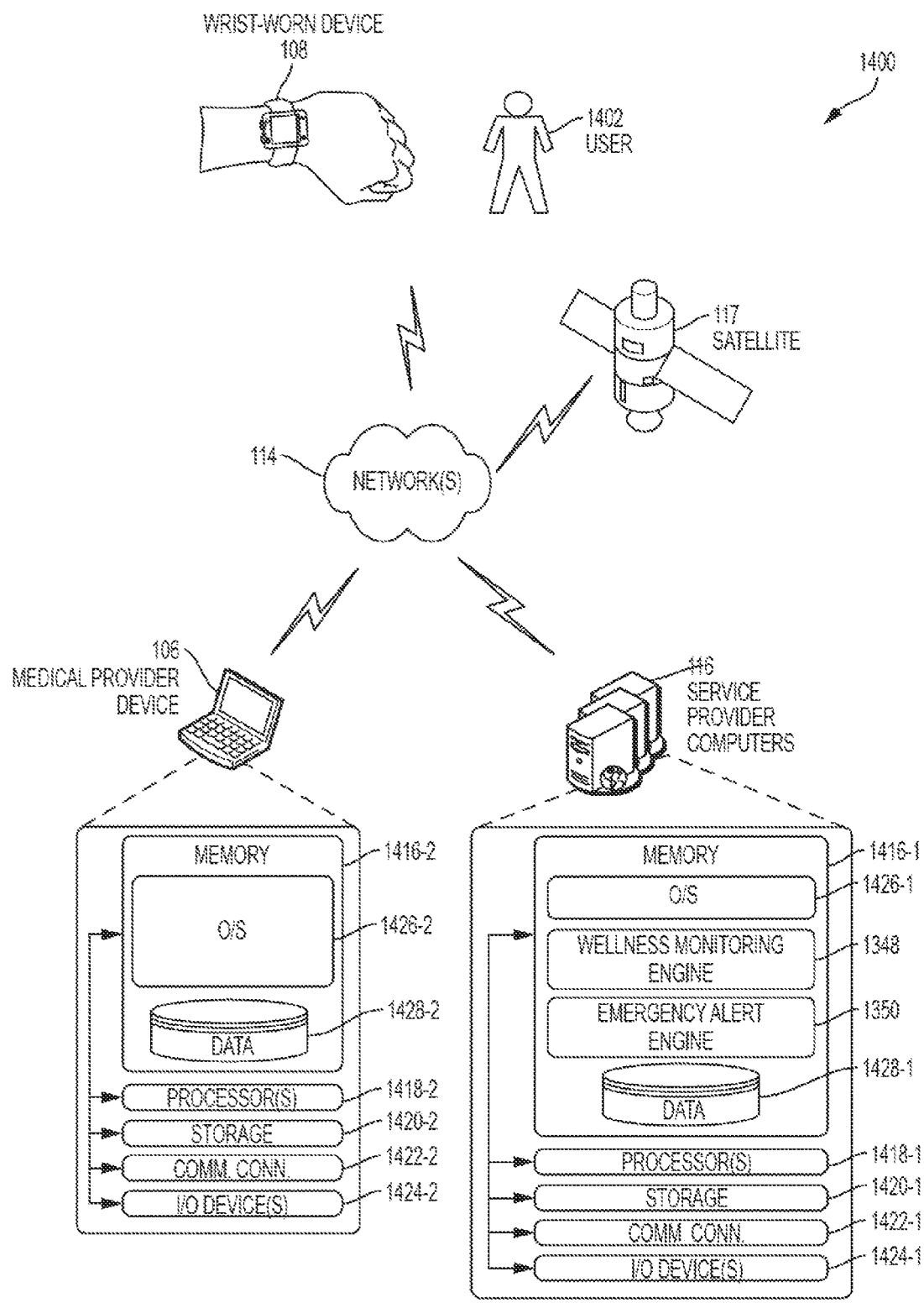
FIG. 14 depicts an example system or architecture for monitoring of a user of the wrist-worn device.

FIG. 14 depicts an example system or architecture 1400 for monitoring wellness of a user of the wrist-worn device 108. In this example, wellness monitoring engine 1348, emergency alert engine 1350, and are depicted as being located on the wrist-worn device 108. In some aspects, additional engines or modules can be located on the wrist-worn device 108, for example, the modules shown in FIG. 1B (e.g., fall detection module 140 location and floor learning module 120, etc.). It should be understood that in some aspects, wellness monitoring engine, emergency alert engine 1350, and/or modules can be located on service provider computers 116, on medical provider device 106, or elsewhere. In architecture 1400, a user 1402 utilizes the wrist-worn device 108 (e.g., a wristband monitoring device 110 and a faceplate device 112) to access various engines (e.g., a wellness monitoring engine 1348, emergency alert engine 1350 via one or more networks 114. In some aspects, the user 1402 utilizes the wrist-worn device 108 to access various engines and modules) via a user interface accessible by the engines. Wellness monitoring engine 1348, emergency alert engine 1350, and fall detection module may each be hosted, managed, and/or provided by a computing resources service or service provider, such as by utilizing one or more service provider computers 116. The one or more service provider computers 116, in some examples, provide computing resources such as, but not limited to, client entities, low latency data storage, durable data storage, data access, management, virtualization, cloud-based software solutions, electronic content performance management, etc. The one or more service provider computers 116 are also operable to provide web hosting, computer application development, and/or implementation platforms, combinations of the foregoing, or the like to the user.

In some examples, the wrist-worn device 108 is in communication with the service provider computers 116 via the networks 114, or via other network connections. Additionally, the wrist-worn device 108 may be part of a distributed system managed by, controlled by, or otherwise part of the service provider computers 116. In some examples, the networks 114 include any one or a combination of many different types of networks, such as cable networks, the Internet, wireless networks, cellular networks and other private and/or public networks. The wrist-worn device 108 is also in communication with SPS satellites 117 for determining the location of the wrist-worn device and assisting in fall detection determinations.

In at least one embodiment, the wellness monitoring engine 1348 allows the user 1401 to interact with the service provider computers 116 or medical provider device 106. The one or more service provider computers 116, perhaps arranged in a cluster of servers or as a server farm, host one or more of the wellness monitoring engine 1348, the emergency alert engine 1350, and/or cloud-based software services. Other server architectures may be used to host the wellness monitoring engine 1348 and/or cloud-based software services. The e is capable of handling requests from a user 1401 and serving, in response, various user interfaces that are rendered at the wrist-worn device 108. The wellness monitoring engine 1348 provides any type of device or application control. The wellness monitoring engine 1348 and/or corresponding control are provided by the operating system 1344 of the wrist-worn device 108 (e.g., on the faceplate device 112). As discussed above, the described techniques can similarly be implemented outside of the wellness monitoring engine 1348, such as with other applications running on the wrist-worn device 108, for example with respect to the emergency alert engine 1350.

In some aspects, the service provider computers 116 and medical provider device 106 are any type of computing devices such as, but not limited to, a mobile phone, a smart phone, a personal digital assistant (PDA), a laptop computer, a desktop computer, a server computer, a thin-client device, a tablet PC, etc. Additionally, it should be noted that in some embodiments, the service provider computers 116 and/or medical provider device 106 are executed by one or more virtual machines implemented in a hosted computing environment. The hosted computing environment may include one or more rapidly provisioned and released computing resources, which computing resources may include computing, networking and/or storage devices. A hosted computing environment is also referred to as a cloud-computing environment.

In one illustrative configuration, the service provider computers 116 and medical provider device 106 each include at least one memory (e.g., the memory 1416-1 and the memory 1416-2) and one or more processing units (e.g., processor(s) 1418-1 and processor(s) 1418-2). The processor(s) 1418-1 and/or the processor(s) 1418-2 are implemented as appropriate in hardware, computer-executable instructions, firmware, or combinations thereof. Computer-executable instruction or firmware implementations of the processor(s) 1418-1 and the processor(s) 1418-2 include computer-executable or machine-executable instructions written in any suitable programming language to perform the various functions described.

In at least one aspect, the memory 1416 and/or the memory 1416-2 store program instructions that are loadable and executable on the processor(s) 1418-1 or the processor(s) 1418-2, respectively, as well as data generated during the execution of these programs. Depending on the configuration and type of service provider computers 116 or medical provider device 106, the memory 1416 and/or the memory 1416-2 may be volatile (such as RAM) and/or non-volatile (such as ROM, flash memory, etc.). The service provider computers 116 and/or the medical provider device 106 also include additional storage (e.g., additional storage 1420-1 and additional storage 1420-2) which includes removable storage and/or non-removable storage. The memory 1416, the memory 1416-2, the additional storage 1420-1, the additional storage 1420-2, both removable and non-removable, are all examples of computer-readable storage media. In at least one aspect, computer-readable storage media include volatile or non-volatile, removable or non-removable media implemented in any method or technology for storage of information such as computer-readable instructions, data structures, program modules, or other data. Additional types of computer storage media that may be present in the service provider computers 116 and/or medical provider device 106 may include, but are not limited to, PRAM, SRAM, DRAM, RAM, ROM, EEPROM, flash memory or other memory technology, CD-ROM, DVD or other optical storage, magnetic cassettes, magnetic tape, magnetic disk storage or other magnetic storage devices, or any other medium which can be used to store the desired information and which can be accessed by the service provider computers 116 and/or medical provider device 106, respectively. Combinations of any of the above should also be included within the scope of computer-readable media.

In accordance with at least one aspect, the service provider computers 116 and/or medical provider device 106 contain communications connection(s) (e.g., 1422-1 and 1422-2) that allow the service provider computers 116 and/or medical provider device 106 to communicate with a stored database, another computing device or server, user terminals and/or other devices on the networks 114. The service provider computers 116 and/or medical provider device 106 also include I/O device(s) 1424-1 and/or I/O device(s) 1424-2, respectively, such as a keyboard, a mouse, a pen, a voice input device, a touch input device, a display, speakers, a printer, etc.

Turning to the contents of the memory (e.g., the memory 1416 and/or the memory 1416-2) in more detail, each memory includes an operating system (e.g., 1426-1 and 1426-2), one or more data stores (e.g., 1428-1 and 1428-2), and/or one or more application programs, modules, or services for implementing the features disclosed herein. For example, medical-related data, sensor data collected from wrist-worn device 108, and any suitable data utilized by wellness monitoring engine 1348 may be stored in data store 1428-1 and/or data store 1428-2.

Figure 15:
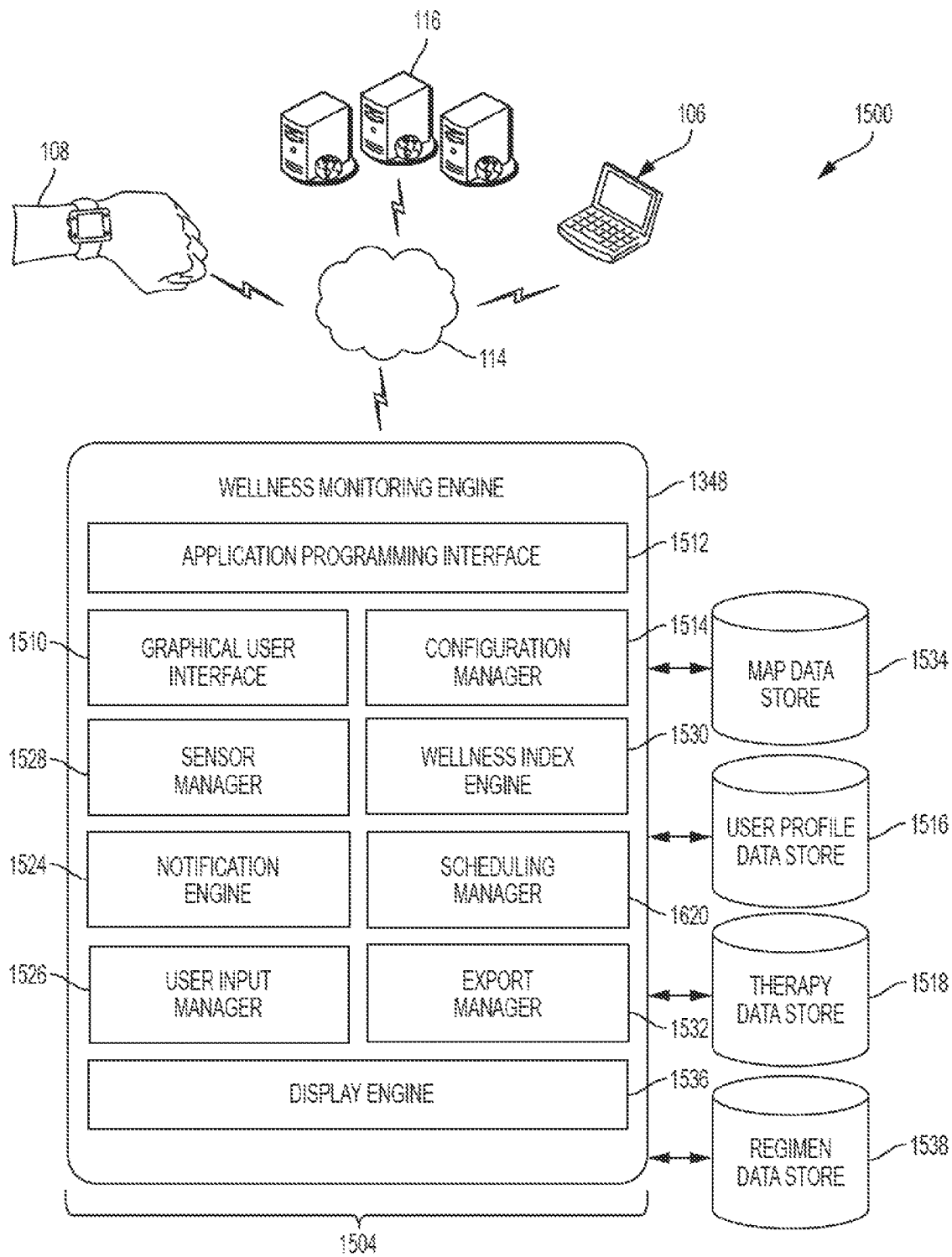
FIG. 15 depicts an example computer architecture for providing a wellness monitoring engine, including a plurality of modules that may carry out various embodiments.

FIG. 15 depicts an example computer architecture 1500 for providing a wellness monitoring engine 1348, including a plurality of modules 1504 that may carry out various embodiments. Wellness monitoring engine 1348 can be provided on wrist-worn device 108, medical provider device 106, service provider computers 116, or on another device in communication with the wrist-worn device 108 via network 114. In at least one embodiment, wellness monitoring engine 1348 is stored on faceplate device 112 or, alternatively, is stored on a server accessible to the faceplate device 112 via network 114. In at least some examples, the modules 1504 are software modules, hardware modules, or a combination thereof. If the modules 1504 are software modules, the modules 1504 are embodied on a computer-readable medium and processed by a processor in any of the computer systems described herein. It should be appreciated that any module or data store described herein, may be, in some embodiments, a service responsible for managing data of the type required to make corresponding calculations. The modules 1504 may be configured in the manner suggested in FIG. 15 or may exist as separate modules or services external to the wellness monitoring engine 1348.

An administrator (e.g., a physician) configures the wellness monitoring engine 1348 via a graphical user interface 1510 the wellness monitoring engine 1348 presented on medical provider device 106. Medical provider device 106 may be any electronic device capable of receiving and transmitting electronic data (e.g., a laptop, a cellphone, another wrist-worn device 108). The configuration information can include, but is not limited to, medical-related data. Once configuration information is entered via graphical user interface 1510, application programming interface 1512, a component of the wellness monitoring engine 1348, is utilized to receive the configuration information.

In accordance with at least one embodiment, configuration manager 1514, a component of the wellness monitoring engine 1348, is configured to receive configuration information. The configuration manager 1514 is responsible for creating and maintaining a user profile utilized to store such configuration information, including therapy or treatment information for the user. Further, the configuration manager 1514 causes such configuration data to be stored in a user profile data store 1516 (e.g., data store 1342 or data store 1428-1). Additionally, or alternatively, configuration manager 1514 interacts with therapy data store 1518, a data store responsible for storing information regarding one or more therapies. In at least one example, the configuration manager 1514 queries therapy data store 1518 for information regarding one or more therapies indicated in the received configuration information. Any information returned from therapy data store 1518 may be stored by the configuration manager 1514 in user profile data store 1516, along with, or separate from, the user profile.

In at least one embodiment, scheduling manager 1520 is configured to receive configuration information from configuration manager 1514, including information pertaining to a prescribed therapy. The prescribed therapy may be associated with a specific therapy stored in the therapy data store 1518. The scheduling manager 1520 is responsible for generating a regimen based on the prescribed therapy. The regimen indicates one or more notifications to be provided to the user at a specific day and/or time. The regimen indicates one or more notifications to be provided to the user at a specific day and/or time. The regimen additionally indicates one or more particular times at which to transmit medical-related information gathered or obtained by the wrist-worn device 108 to service provider computers 116. In at least one example, scheduling manager 1520, according to the generated regimen, causes notification engine 1524 to provide one or more electronic notifications on the wrist-worn device 108. The notification may include, but is not limited to, a sensor reading request, to take a dosage of medication, or to conduct a form of exercise.

In at least one embodiment, user input manager 1526 is configured to present questions to the user via faceplate device 112 of wrist-worn device 108. In at least one example, scheduling manager 1520 determines one or more questions to be posed to the user at a particular time in accordance with the generated regimen. A "regimen," as used herein, includes a schedule for one or more therapies that specifies various times in which to conduct various actions associated with the therapy. In the case where the regimen specifies that a question should be posed to the user, scheduling manager 1520 causes user input manager 1526 to pose the determined question(s) to the user via faceplate device 112 at the appropriate time. The user utilizes faceplate device 112 to respond to the question(s). Upon receipt of the response, user input manager 1526 stores such response data in user profile data store 1516 (e.g., data store 1342, or 1428-1). Additionally, user input manager 1526 causes scheduling manager 1520 to act upon the response in one or more ways based on the therapy implemented. In one example, scheduling manager 1520, determining that it is time for the user to take a sensor reading, causes notification engine 1524 to present a reminder to the user on faceplate device 112. The user input manager 1526 sends to the device a question such as "are you ready to get your blood pressure taken?" The user responds affirmatively or negatively. Alternatively, the user, having had no question posed, affirmatively initiates, via faceplate device 112, a sensor reading. Either or both user inputs are received by user input manager 1526. Additionally, such user input is stored in user profile data store 1516 and is forwarded to scheduling manager 1520. Scheduling manager 1520, in response to such user input, updates the regimen.

In at least one example, scheduling manager 1520 causes user input manager 1526 to pose a question to the user via faceplate device 112. For instance, scheduling manager 1520 determines that a question ought to be posed to the user at a particular time, or because of a particular response. For instance, the regimen may specify that the user be asked, "Are you feeling light-headed?" an hour after the user has indicated that he took his medication. In such a case, scheduling manager 520 causes user input manager 1526 to present the question to the user via faceplate device 112. The user responds to the question via faceplate device 112 and such response is received by user input manager 1526, stored in user profile data store 1516 (e.g., data store 1342 or data store 1428-1), and/or forwarded to scheduling manager 1520. In at least one embodiment, scheduling manager 1520 updates the regimen based on the response. For example, the therapy may indicate that, if the user responds that he does, in fact, feel light-headed when asked (e.g., an hour after taking his medication), the regimen be altered in some way (e.g., by increasing or decreasing the medication dosage). In at least one example, the regimen is altered such that the user is immediately prompted to take an additional dosage. Furthermore, the regimen is updated by the scheduling manager 1520 to reflect changes brought on by the received user input. The regimen may be stored on regimen data store 1538 or any suitable data store configured to store such information. Regimen data store 1538 may include as a component of wellness monitoring engine 1348 or as a data store remote to wellness monitoring engine 1348.

In response to input provided by the user, or based on a pre-programmed regime, the scheduling manager 1520 can cause sensor manager 1528, a component of wellness monitoring engine 1348, to activate one or more sensors located on the wrist-worn device 108. Sensor manager 1528 communicates with the one or more sensors to cause vital sign information to be collected. For instance, in the ongoing example, sensor manager 1528 causes a heart rate sensor to be activated. The sensor manager 1528 is configured to receive data from the heart rate sensor. The sensor manager 1528 further causes the heart rate information to be stored in user profile data store 1516 and/or forwards the heart rate information to the scheduling manager 1520 for analysis. Sensor manager 1528, additionally or alternatively, activates blood pressure sensor. The sensor manager 1528 is configured to receive data from the blood pressure sensor. The sensor manager 1528 causes the blood pressure sensor to be stored in user profile data store 1516 and/or forwards the blood pressure information to the scheduling manager 1520. Scheduling manager 1520, as discussed above, analyzes the heart rate information and/or the blood pressure information to determine any regimen modification(s) necessary in accordance with the therapy. Though a heart rate sensor and a blood pressure sensor are used in this example, it should be appreciated that any sensor, or combination of sensors, located on the wrist-worn device 108 may be utilized, in any suitable order, via a similar manner as described above.

In at least one embodiment, another user, for example a physician or emergency medical personnel, may access medical-related data stored in memory 1416 of service provider computers 116 or other information contained on and/or recorded by wrist-worn device 108. For example, in an emergency situation, another user can access medical allergy information of the user. Additionally, or alternatively, someone other than the user may access information recorded by the wrist-worn device 108. As an example, a physician can enable medical-related data to be displayed on the faceplate device 112 or a display of another device. The activation of such a setting is received by the user input manager 1526. The user input manager 1526 accesses user profile data store 1516 to obtain medical-related data for the user. The user input manager 1526 can then display such information on the faceplate device 112 and/or enable the physician to access such information at a remote location (e.g., via a website presented on the medical provider device 106 or other computing device).

In accordance with at least one embodiment, wellness index engine 1530, a component of wellness monitoring engine 1348, is responsible for calculating a wellness index for the patient. The wellness index, as described above, is a numerical value that indicates an overall wellness value for the patient. The wellness index engine 1530 may be configured to receive, or otherwise obtain, at least one of sensor data, therapy data, regimen, or user input, from any combination of the modules discussed above. Therapy data may include information related to normal sensor data ranges (e.g., a normal Heart Rate range, normal glucose level). Such normal sensor data ranges may be based on age, sex, race, or other suitable demographic information. Upon receipt, or at a suitable time, the wellness index engine 1530 may calculate a wellness index based on the sensor data, therapy data, regimen data, and user input and store the calculated value in user profile data store 1516. The wellness index may be calculated using various weights for the sensor data and user input or each may be weighed the same for purposes of the calculation. In at least one example, the wellness index may be calculated with sensor readings based at least in part on the inverse value of a deviation from a set of standard sensor readings taken from normal populations. Additionally, or alternatively, the wellness index may normalized to a score between 0 and 10. In at least one example, wellness index engine 1530 may interact with user profile data store 1516 to retrieve information regarding medical-related data of other users. For example, the wellness index engine 1530 may take into account other users blood pressure readings, for example, when determining how much to weigh the user's blood pressure reading. Wellness index engine 1530 may take into account all other users, or a subset of the other users. For example, wellness index engine 1530 may compare the user's blood pressure readings to other user's under the same proscribed therapy, while ignoring medical-related data of users that are not under the same prescribed therapy.

Wellness index engine 1530 may be configured to cause export manager 1532 to transmit the wellness index to wrist-worn device 108, the medical provider device 106, service provider computers 116, or any suitable electronic device located away from wellness monitoring engine 1348.

In at least one embodiment, display engine 1536, a component of wellness monitoring engine 1348, may be configured to interact with map data store 1534 in order to display a map of a geographical location (e.g., a hospital ward floor plan, assisted living home floor plan, a region map, a state map). In at least one example, the display engine 1536 may cause a floor plan of a hospital ward to be displayed, for example, on medical provider device 106), with, in some cases, at least one graphical element (e.g., a colored dot) superimposed over the floor plan indicating a location and wellness index generated by a wrist-worn device (e.g., a wrist-worn device worn by a patient of the hospital).

Figure 16:
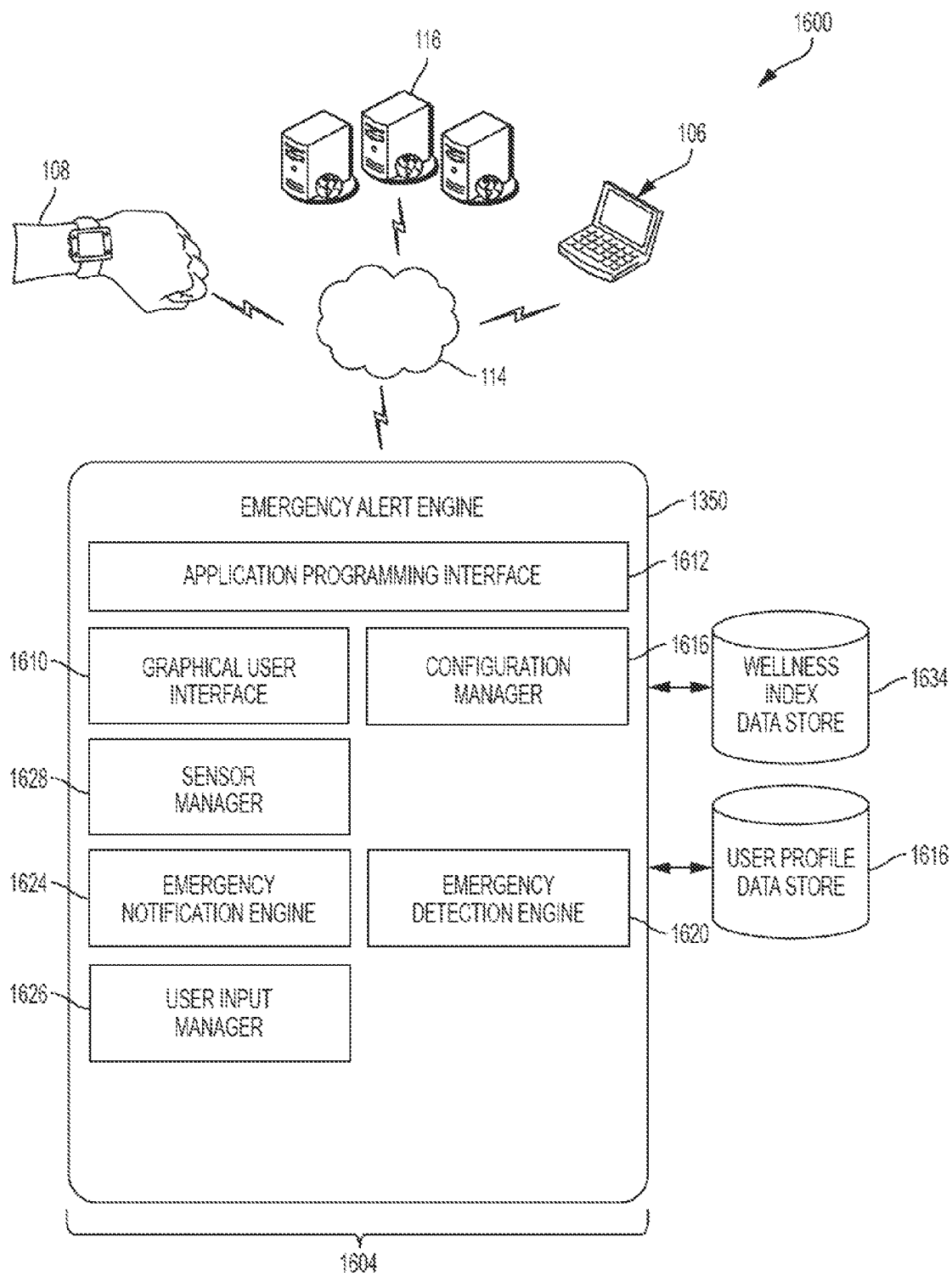
FIG. 16 depicts an example computer architecture for providing an emergency alert engine, including a plurality of modules that may carry out various embodiments.

FIG. 16 depicts an example computer architecture 1600 for providing an emergency alert engine 1350, including a plurality of modules 1604 that may carry out various embodiments. Emergency alert engine 1350 can be provided on wrist-worn device 108, medical provider device 106, service provider computers 116, or on another device in communication with the wrist-worn device 108 via network 114. In at least some examples, the modules 1604 are software modules, hardware modules, or a combination thereof. If the modules 1604 are software modules, the modules 1604 are embodied on a computer-readable medium and processed by a processor in any of the computer systems described herein. It should be appreciated that any module or data store described herein, may be, in some embodiments, a service responsible for managing data of the type required to make corresponding calculations. The modules 1604 may be configured in the manner suggested in FIG. 16 or may exist as separate modules or services external to the emergency alert engine 1350.

In accordance with at least one embodiment, a method is enabled for emergency monitoring and alerting using a wrist-worn device (e.g. wrist-worn device 108). For example, the emergency alert engine 1350 may be a component of the faceplate device 112, wristband monitoring device 110, or service provider computers 116, respectively. In at least one embodiment, emergency alert engine 1350 is stored on the wrist-worn device 108 or, alternatively, is stored on a server accessible to the wrist-worn device 108 via network 114.

An administrator (e.g., a physician) configures the emergency alert engine 1350 via a graphical user interface 1610 the emergency alert engine 1350 presented on medical provider device 106. Medical provider device 106 may be any electronic device capable of receiving and transmitting electronic data (e.g., a laptop, a cellphone, another wrist-worn device 108). The configuration information can include, but is not limited to, medical-related data. Once configuration information is entered via graphical user interface 1610, application programming interface 1612, a component of the emergency alert engine 1350, is utilized to receive the configuration information.

In accordance with at least one embodiment, configuration manager 1614, a component of the emergency alert engine 1350, is configured to receive configuration information. The configuration manager 1614 is responsible for creating and maintaining a user profile utilized to store such configuration information, including therapy or treatment information for the user, emergency contact information of the user, and medical data related to the user. Further, the configuration manager 1614 causes such configuration data to be stored in a user profile data store 1616 (e.g., data store 1342, data store 1428-1, data store 1516). Additionally, or alternatively, configuration manager 1614 interacts with wellness index data store 1634, a data store responsible for storing information regarding the wellness index of the user gathered by the wellness monitoring engine 1348. In at least one example, the configuration manager 1614 queries wellness index data store 1634 for information regarding the current or previous wellness indexes of the user. The user profile of a user can also store data indicating a range of wellness indexes that indicates an emergency. In some embodiments, the user profile can include a minimum value, maximum value, or value range, associated with a particular sensor (e.g. heart rate monitor or blood pressure monitor) that can indicate an emergency.

In accordance with at least one embodiment, an emergency detection engine 1620, a component of the emergency alert engine 1350, is configured to determine if an emergency is affecting the user. The emergency detection engine 1620 is configured to receive user profile data from user profile data store 1616 and the wellness index data store 1634. The emergency detection engine 1620 can retrieve a current wellness index of the user that has been saved to wellness index data store 1634 by the wellness monitoring engine 1348. In some embodiments, the emergency detection engine 1620 receives a current wellness index of the user directly from the wellness monitoring engine 1348. The emergency detection engine 1620 can compare the current wellness index to a minimum wellness index associated with the user profile to determine if the current wellness index indicates an emergency is affecting the user. In at least one embodiment, the emergency detection engine 1620 causes emergency notification engine 1624 to generate and transmit an alert notification in response to determining the current wellness index falls at or a below a minimum wellness index that indicates an emergency is affecting the user.

Consider the case where the user's heart rate drops dangerously low, or even stops. The wellness monitoring engine 1348 can receive such information and determine that the wellness index is a value of 1 and can transmit that information to the emergency detection engine 1620 or can save the wellness index to the wellness index data store 1634. The emergency detection engine 1620 can retrieve the wellness index from the wellness index data store 1634 or can receive the wellness index from the wellness monitoring engine 1348. The emergency detection engine 1620 can determine that the wellness index is less than a minimum wellness index of 4 associated with the user's profile in the user profile data store.

The emergency detection engine 1620 can cause the emergency notification engine 1624 to generate and transmit an alert notification. The emergency notification engine 1624 can access the user profile data store 1616 (e.g., data store 1342, 1428-1, 1516) for user profile data. User profile data indicates physician contact information, emergency contact information, and/or emergency personnel, for example. If the user profile data includes such information, the notification engine 1624 may cause a notification to be sent to the indicated physician/emergency contact/emergency personnel.

In at least one embodiment, the emergency detection manager 1620 can receive an indication from a fall detection module located on the wrist-worn device (see FIG. 1B) that the user has experienced a fall. In some embodiments, the fall detection module can update the user's profile to reflect a fall was detected on a specific date and time. The emergency detection manager 1620 can retrieve the updated user profile data indicating a fall was detected. In response to reviving an indication from the fall detection module or retrieving the user profile data indicating a fall was detected, the emergency detection engine 1620 can cause the emergency notification engine 1624 to generate and transmit an alert notification.

In at least one embodiment, the emergency detection engine 1620 is configured to detect the activation of an emergency indicator by the user. In some embodiments the emergency indicator can be a button located on the faceplate device 112 or the wrist band 110 of the wrist-worn device 108 that can be pressed by the user to indicate the user is experiencing an emergency. In some embodiments, the emergency detector is another user interface. In response to detecting the activation of the emergency indicator, the emergency detection engine 1620 can cause the emergency notification engine 1624 to generate and transmit an alert notification.

In some aspects, the emergency detection manager 1620 can cause a sensor manager 1628 to activate one or more sensors located on the wrist-worn device 108. Sensor manager 1628 communicates with the one or more sensors to cause vital sign information to be collected. For instance, in the ongoing example, sensor manager 1628 can cause a heart rate sensor to be activated. The sensor manager 1628 is configured to receive data from the heart rate sensor. The sensor manager 1628 further causes the heart rate information to be stored in user profile data store 1616 and/or forwards the heart rate information to the emergency notification engine 1624 for inclusion in the alert notification. Though a heart rate sensor is used in this example, it should be appreciated that any sensor, or combination of sensors, located on the wrist-worn device 108 may be utilized, in any suitable order, via a similar manner as described above.

The emergency notification engine 1624 can generate and transmit an alert notification. The alert notification can be an automated phone call, email message, text message, or other suitable form of communication. The alert notification can be sent via a network 114, for example a Wi-Fi network, a cellular network, or other communication network. In some embodiments of the present disclosure the emergency notification engine 1624 is configured to determine the strength of the various networks 114 available to the wrist-worn device 108. The emergency notification engine 1624 can determine the format of the notification (e.g., text message, e-mail message, data message, or voice call) based on factors including the severity or type of emergency (e.g., a fall detected, an emergency indicator activated, a wellness index falling below a pre-set threshold) and the strength of the various communication networks. The emergency notification engine 1624 can also determine which communication network to use to transmit the notification. In some embodiments the emergency notification engine 1624 selects a communication network based on factors that can include the strength of the various communication networks, the type and/or severity of the emergency, and the power level of the wrist-worn device. The emergency notification engine 1624 can determine the format of the alert notification and the communication network for transmission that can present the highest chance of successful transmission of the alert notification.

In one embodiment, the emergency notification engine 1624 can determine that an alert notification will be transmitted via a cellular network when there is no Wi-Fi network available or the signal of the Wi-Fi network available is below a pre-set signal strength. The emergency notification engine 1624 can also repeatedly re-transmit an alert notification (for example an SMS text message alert) continuously until the emergency notification engine 1624 receives confirmation that the alert notification was successfully sent and/or received. The emergency notification engine 1624 can receive confirmation that the alert was successfully transmitted from the wireless communication interface 1304. In some aspects, the emergency notification engine 1624 can transmit the alert notification a pre-determined number of times based on the strength of the signal of the communication network used to transmit the alert notification, the type of the emergency, and/or the power level of the wrist-worn device 108.

Additionally, or alternatively, the emergency notification engine 1624 can also transmit additional data related to the user (e.g., sensor data, user profile data, GPS location data). In one example, upon determining the existence of an emergency condition, the sensor manager 1628 causes the GPS sensor 1320 to activate to ascertain the user's location. Any other sensor, or combination of sensors, included on the device may be similarly activated. Information collected by the sensor(s) is received by the sensor manager 1628. The sensor manager 1628 can relay the information to the emergency notification engine 1624. Emergency notification engine 1624 may then report such information away from the device in a manner similar to that described above.

Consider the example in which the wellness index engine 1530 calculates a wellness index of 4 based on the sensor data indicating the user has slightly high blood pressure and a slightly elevated body temperature. The wellness index engine 1530 can transmit the current wellness index to the user profile data store 1634, in some aspects including a timestamp. The emergency detection engine 1620 can access the current wellness index stored in the wellness index data store 1634. The emergency detection engine 1620 can access a minimum wellness value stored in the user profile data store 1634. The minimum wellness value can indicate a wellness index that is indicative of the lowest wellness index a patient may have without triggering an emergency notification. In said example, the emergency detection engine 1620 can determine that the current wellness index of 4 is less than the minimum wellness of 5. The emergency notification engine 1624 can transmit a request to the notification engine 1624 to generate and transmit an alert notification.

Emergency notification engine 1624 can determine that a strong cellular network signal is available and a weak Wi-Fi signal is available. Based on the wellness index of 4 and the strength of the cellular/Wi-Fi signals, the emergency notification engine 1624 can determine that the alert notification should be sent as a text message on the cellular network to increase the chances the alert notification is successfully transmitted. The notification engine can generate the alert notification and instruct the wireless communication interface 1304 to transmit the alert notification via the cellular network.

In an example in which the wellness index engine 1530 receives sensor data from a heart rate sensor indicating the user's heart rate has dropped to nearly zero, the wellness index engine 1530 can calculate a wellness index of 1 and transmit the current wellness index to the user profile data store 1516. The emergency detection engine 1620 can access the current wellness index stored in the user profile data store 1534 and determine the current wellness index is below a minimum wellness value. The emergency detection engine 1620 can cause the emergency notification engine 1624 to generate and transmit an alert notification. The emergency notification engine 1624 can determine that a strong cellular network signal is available and a weaker Wi-Fi network signal is available. The emergency notification engine 1624 can determine the severity of the emergency by comparing the wellness index to a critical wellness index. For example, the user profile can contain a critical emergency wellness index that can be compared to the wellness index to determine if the emergency is a critical emergency. Based on the wellness index of 1 being less than the critical emergency wellness index of 3, the emergency notification engine 1624 can determine that the alert notification should be send as a text message via the cellular network. The lower bandwidth requirements of the SMS can create a higher likelihood of a successful transmission. The SMS alert notification format can also allow the emergency notification engine 1624 repeatedly send over the cellular network until the emergency notification engine 1624 receives confirmation from the wireless communication interface 1304 that the alert notification was successfully transmitted and/or was successfully received at the destination.

In some aspects, the emergency notification engine 1624 can make a determination regarding the method of transmission of the alert notification and/or the number of transmissions based on the severity of the emergency and/or the signal strength of the communication networks available. In some aspects, the emergency notification engine 1624 can also consider the power-level of the wrist-worn device 108 in determining the method of transmission and format of the alert notification. The severity of the emergency can be determined based on the type of emergency and additional sensor data or user profile data. For example, in response to determining the user has experienced a fall, additional sensor data can be collected (e.g., blood pressure data), and input from the user can be collected (e.g., input of "yes" response from user following a query of "have you fallen?") to determine the severity index of the emergency.

Figure 17:
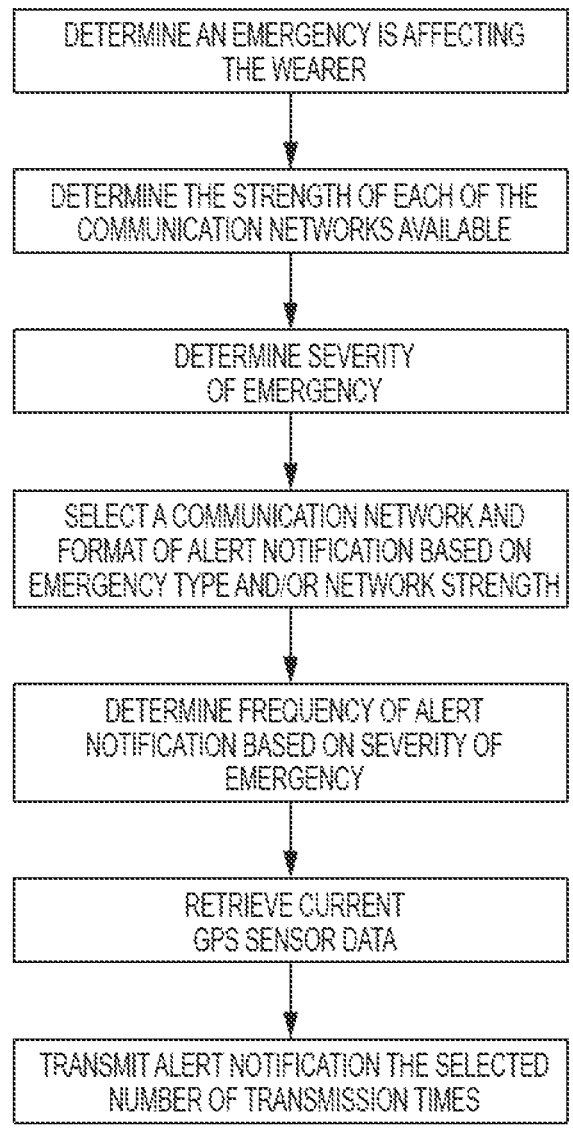
FIG. 17 depicts a block diagram of an example method for using the emergency alert engine.

FIG. 17 depicts a block diagram 1700 of an example method for using the emergency alert engine 1350, in accordance with at least one embodiment. The emergency alert engine 1350 can receive a current wellness index of the wearer or retrieve from the user profile a current wellness index of the wearer of the wrist-worn device 108. The emergency alert engine 1350 can compare the current wellness index to a pre-set minimum value indicative of a non-emergency status of the wearer. At 1702 the emergency alert engine 1350 can determine that the current wellness index is below the minimum value. In response to determining the current wellness index is below the minimum value the emergency alert engine 1350 can determine an alert notification is to be sent. At 1704 emergency alert engine 1350 can determine the strength of each of the communication networks available to the engine for transmitting the alert notification.

The emergency alert engine 1350 can also determine the severity or type of the emergency affecting the wearer at step 1706. For example, the emergency alert engine 1350 can determine the emergency was a fall detected by a fall detection module, an activated emergency indicator, or a current wellness index that is below a minimum value. Where the emergency is detected based on the current wellness index, the current wellness index can itself be used to determine the severity of the emergency. In aspects where the emergency is based on the activation of the emergency indicator, the emergency alert engine can determine a severity index of the emergency based on additional information, for example user input collected from the user following the activation of the emergency indicator (e.g., a "yes" response to a query asking "are you experiencing an emergency") and/or sensor data collected proximate to the time of the activation of the emergency indicator. In aspects in which the emergency is based on a fall being detected, the severity index can be determined based on additional information that can include recent sensor data, the likelihood of a fall having occurred, and/or user input (e.g. a "yes" response to a query asking "have you fallen?"). The severity index can reflect the severity of the emergency and can further be used to determine the format and communication network for the alert notification.

At 1708 the emergency alert engine can select a communication network and form of the alert notification based on the strength of the communication networks, the severity of the emergency, and/or the power level of the device. At 1710 the emergency alert engine can determine how many emergency alert notifications to transmit. For example, when the severity of the emergency is high and the strength of the selected communication network is low, the emergency alert engine can continue to transmit the alert notification until the emergency alert engine receives confirmation that the notification was successfully transmitted. In some aspects, the emergency alert engine can transmit the alert notification a pre-selected number of times based on the strength of the communication network and/or the severity of the emergency.

At 1712 the emergency alert engine can retrieve current GPS sensor data from the wrist-worn device. In some aspects, the emergency alert engine can retrieve current GPS sensor data that has been stored in the user profile data store. When the GPS sensor data stored in the user profile data store is not within a pre-determine period of time since the emergency alert engine determined an emergency was affecting the user, the engine can instruct a sensor manager to activate the GPS sensor to gather current GPS sensor data.

At 1714 the emergency alert engine can transmit the alert notification on the selected network. The alert notification can include the current GPS sensor data that can provide detailed information on the location of the wearer. In some aspects, the alert notification can also contain information related to the emergency, for example, the sensor data collected in determining the wellness index, if a fall was detected, or if the user activated the emergency indicator. In some aspects, additional information gathered from the sensors, the user profile, or other sources can be transmitted in a separate notification. The emergency alert engine can transmit the notification the select number of times on the selected communication network. In some aspects, the emergency alert engine can continue to transmit the alert notification until the emergency alert engine receives confirmation that the notification was successfully transmitted.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps, and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine-readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodied instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read-only memory (ROM), random access memory (RAM), magnetic RAM, core memory, magnetic disk storage mediums, optical storage mediums, flash memory devices and/or other machine-readable mediums for storing information. The term "machine-readable medium" includes, but is not limited to, portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A wrist-worn device for facilitating emergency detection and alert transmission, the wrist-worn device, comprising:
   a first sensor configured to generate elevation data that represents an elevation of the wrist-worn device;
   a second sensor configured to generate acceleration data that represents a magnitude of acceleration of the wrist-worn device;
   one or more processors; and
   one or memories coupled with said one or more processors, wherein the one or more processors and one or more memories are configured to:
   determine, based on the elevation data, an elevation of a surface;
   detect a fall affecting a wearer of the wrist-worn device based on the elevation data and the acceleration data;
   determine a signal strength of one or more communication networks available to the wrist-worn device;

select a preferred communication network for transmitting an alert notification based on the signal strength of the one or more communication networks;
generate the alert notification; and
transmit the alert notification away from the wrist-worn device using the preferred communication network;
wherein detecting the fall includes:
determining that the acceleration data satisfies a fall condition; and
determining, based on the elevation data, that the wrist-worn device is vertically displaced from the surface by a distance that passes a threshold distance.

2. The wrist-worn device of claim 1, the one or more processors and one or more memories being further configured to:
cause a sensor on the wrist-worn device to collect vital sign information in response to determining that a wellness index is below a pre-set threshold; and
receive the vital sign information,
wherein the alert notification includes the vital sign information.

3. The wrist-worn device of claim 2, the one or more processors and one or more memories being further configured to:
determine a number of times to transmit the alert notification based on the signal strength of the selected communication and the wellness index.

4. The wrist-worn device of claim 1, wherein the preferred communication network is a cellular network and the alert notification is one of an SMS message or a voice call.

5. The wrist-worn device of claim 1, wherein the sensor on the wrist-worn device is at least one of a thermometer, a pedometer, a blood pressure monitor, a heart rate sensor, a blood-oxygen level sensor, or a glucose monitor.

6. The wrist-worn device of claim 1, the one or more processors and one or more memories are further configured to:
retrieve recent GPS sensor data and wherein the alert notification includes the recent GPS sensor data.

7. The wrist-worn device of claim 1, the one or more processors and one or more memories are further configured to:
cause a GPS sensor on the wrist-worn device to generate current GPS sensor data in response to determining the wellness index is below a pre-set threshold,
wherein the current GPS sensor data is associated with a location of the wrist-worn device and the alert notification includes the current GPS sensor data.

* * * * *